(12) United States Patent
Euteneuer et al.

(10) Patent No.: US 12,059,188 B2
(45) Date of Patent: *Aug. 13, 2024

(54) METHODS AND APPARATUS FOR DEPLOYING SHEET-LIKE MATERIALS

(71) Applicant: Rotation Medical, Inc., Plymouth, MN (US)

(72) Inventors: Charles L. Euteneuer, St. Michael, MN (US); Rebecca McCarville, Spring Park, MN (US); Duane Frion, Brooklyn Center, MN (US); Nathaniel Zenz-Olson, Blaine, MN (US); Diane M. Feehan, Corcoran, MN (US); John Quackenbush, Saint Paul, MN (US)

(73) Assignee: Rotation Medical, Inc.

( * ) Notice: Subject to any disclaimer, the term of this patent is extended or adjusted under 35 U.S.C. 154(b) by 0 days.

This patent is subject to a terminal disclaimer.

(21) Appl. No.: 18/212,973

(22) Filed: Jun. 22, 2023

(65) Prior Publication Data

US 2023/0329766 A1    Oct. 19, 2023

Related U.S. Application Data

(63) Continuation of application No. 17/879,683, filed on Aug. 2, 2022, now Pat. No. 11,723,706, which is a (Continued)

(51) Int. Cl.
*A61B 17/88* (2006.01)
*A61B 17/064* (2006.01)
(Continued)

(52) U.S. Cl.
CPC ...... *A61B 17/8872* (2013.01); *A61B 17/0642* (2013.01); *A61B 17/0682* (2013.01);
(Continued)

(58) Field of Classification Search
CPC ............ A61B 17/0642; A61B 17/0682; A61B 2017/303; A61B 17/88; A61B 17/8872;
(Continued)

(56) References Cited

U.S. PATENT DOCUMENTS 511,238 A    12/1893  Hieatzman et al.
765,793 A    7/1904   Ruckel
(Continued)

FOREIGN PATENT DOCUMENTS

CA    2390508 A1    5/2001
EP    0142225 A1    5/1985
(Continued)

OTHER PUBLICATIONS

Alexander et al., "Ligament and tendon repair with an absorbable polymer-coated carbon fiber stent", Bulletin of the Hospital for Joint Diseases Orthopaedic Institute, vol. 46, No. 2, pp. 155-173, 1986.
(Continued)

*Primary Examiner* — Larry E Waggle, Jr.
(74) *Attorney, Agent, or Firm* — Seager, Tufte & Wickhem LLP

(57) ABSTRACT

Implant delivery systems for delivering sheet-like implants include a delivery shaft, an implant expander, a sheath, and a sheet-like implant. In some embodiments, the delivery shaft has a proximal end and a distal end. The implant expander is mounted to the distal end of the delivery shaft. The implant expander includes a central portion and a plurality of leg portions radiating from the central portion. The implant expander is evertable between an unstressed configuration in which a distal surface of the implant expander defines a concave surface, and a first compact configuration in which the distal surface of the implant expander defines a convex surface. The implant expander has a first lateral extent when the implant expander is free to
(Continued)

assume the unstressed configuration. The sheath defines a lumen having a lumen diameter. At least a portion of the delivery shaft is slidably disposed in the lumen. The lumen diameter is smaller than the first lateral extent of the implant expander so that the sheath holds the implant expander in the first compact configuration when slidably disposed therein. The sheet-like implant overlays at least a portion of the distal surface of the implant expander with portions of the sheet-like implant extending between the leg portions of the implant expander and the sheath. Methods of treating a rotator cuff of a shoulder are also disclosed.

20 Claims, 24 Drawing Sheets

Related U.S. Application Data continuation of application No. 17/121,258, filed on Dec. 14, 2020, now Pat. No. 11,413,082, which is a continuation of application No. 16/136,790, filed on Sep. 20, 2018, now Pat. No. 10,881,441, which is a continuation of application No. 14/883,105, filed on Oct. 14, 2015, now Pat. No. 10,085,785, which is a continuation of application No. 12/794,673, filed on Jun. 4, 2010, now Pat. No. 9,179,961.

(60) Provisional application No. 61/313,116, filed on Mar. 11, 2010, provisional application No. 61/184,198, filed on Jun. 4, 2009.

(51) Int. Cl.
*A61B 17/068* (2006.01)
*A61F 2/00* (2006.01)
*A61F 2/08* (2006.01)
*A61B 17/30* (2006.01)

(52) U.S. Cl.
CPC ............ *A61B 17/88* (2013.01); *A61F 2/0063* (2013.01); *A61F 2/0811* (2013.01); *A61B 2017/303* (2013.01); *A61F 2002/0072* (2013.01); *A61F 2/08* (2013.01)

(58) Field of Classification Search
CPC ............ A61F 2/0063; A61F 2002/0072; A61F 2/0811
See application file for complete search history.

(56) References Cited

U.S. PATENT DOCUMENTS

| | | |
|---|---|---|
| 1,728,316 A | 9/1929 | Von Wachenfeldt et al. |
| 1,855,546 A | 4/1932 | File |
| 1,868,100 A | 7/1932 | Goodstein |
| 1,910,688 A | 5/1933 | Goodstein |
| 1,940,351 A | 12/1933 | Howard |
| 2,034,785 A | 3/1936 | Wappler |
| 2,075,508 A | 3/1937 | Davidson |
| 2,131,321 A | 9/1938 | Hart |
| 2,158,242 A | 5/1939 | Maynard |
| 2,199,025 A | 4/1940 | Conn |
| 2,201,610 A | 5/1940 | Dawson, Jr. |
| 2,254,620 A | 9/1941 | Miller |
| 2,277,931 A | 3/1942 | Moe |
| 2,283,814 A | 5/1942 | La Place |
| 2,316,297 A | 4/1943 | Southerland et al. |
| 2,421,193 A | 5/1947 | Gardner |
| 2,571,813 A | 10/1951 | Austin |
| 2,630,316 A | 3/1953 | Foster |
| 2,684,070 A | 7/1954 | Kelsey |
| 2,744,251 A | 5/1956 | Vollmer |
| 2,790,341 A | 4/1957 | Keep et al. |
| 2,817,339 A | 12/1957 | Sullivan |
| 2,825,162 A | 3/1958 | Flood |
| 2,881,762 A | 4/1959 | Lowrie |
| 2,910,067 A | 10/1959 | White |
| 3,068,870 A | 12/1962 | Levin |
| 3,077,812 A | 2/1963 | Dietrich |
| 3,103,666 A | 9/1963 | Bone |
| 3,123,077 A | 3/1964 | Alcamo |
| 3,209,754 A | 10/1965 | Brown |
| 3,221,746 A | 12/1965 | Noble |
| 3,470,834 A | 10/1969 | Bone |
| 3,527,223 A | 9/1970 | Shein |
| 3,570,497 A | 3/1971 | Lemole |
| 3,577,837 A | 5/1971 | Bader, Jr. |
| 3,579,831 A | 5/1971 | Stevens et al. |
| 3,643,851 A | 2/1972 | Green et al. |
| 3,687,138 A | 8/1972 | Jarvik |
| 3,716,058 A | 2/1973 | Tanner, Jr. |
| 3,717,294 A | 2/1973 | Green |
| 3,733,934 A | 5/1973 | Stevenson |
| 3,757,629 A | 9/1973 | Schneider |
| 3,777,538 A | 12/1973 | Weatherly et al. |
| 3,837,555 A | 9/1974 | Green |
| 3,845,772 A | 11/1974 | Smith |
| 3,875,648 A | 4/1975 | Bone |
| 3,960,147 A | 6/1976 | Murray |
| 3,976,079 A | 8/1976 | Samuels et al. |
| 4,014,492 A | 3/1977 | Rothfuss |
| 4,127,227 A | 11/1978 | Green |
| 4,259,959 A | 4/1981 | Walker |
| 4,263,903 A | 4/1981 | Griggs |
| 4,265,226 A | 5/1981 | Cassimally |
| 4,317,451 A | 3/1982 | Crewin et al. |
| 4,400,833 A | 8/1983 | Kurland |
| 4,422,567 A | 12/1983 | Haynes |
| 4,454,875 A | 6/1984 | Pratt et al. |
| 4,480,641 A | 11/1984 | Failla et al. |
| 4,485,816 A | 12/1984 | Krumme |
| 4,526,174 A | 7/1985 | Froehlich |
| 4,549,545 A | 10/1985 | Levy |
| 4,570,623 A | 2/1986 | Ellison et al. |
| 4,595,007 A | 6/1986 | Mericle |
| 4,624,254 A | 11/1986 | McGarry et al. |
| 4,627,437 A | 12/1986 | Bedi et al. |
| 4,632,100 A | 12/1986 | Somers et al. |
| 4,635,637 A | 1/1987 | Schreiber |
| 4,669,473 A | 6/1987 | Richards et al. |
| 4,696,300 A | 9/1987 | Anderson |
| 4,719,917 A | 1/1988 | Barrows et al. |
| 4,738,255 A | 4/1988 | Goble et al. |
| 4,741,330 A | 5/1988 | Hayhurst |
| 4,762,260 A | 8/1988 | Richards et al. |
| 4,799,495 A | 1/1989 | Hawkins et al. |
| 4,809,695 A | 3/1989 | Gwathmey et al. |
| 4,851,005 A | 7/1989 | Hunt et al. |
| 4,858,608 A | 8/1989 | McQuilkin |
| 4,884,572 A | 12/1989 | Bays et al. |
| 4,887,601 A | 12/1989 | Richards |
| 4,924,866 A | 5/1990 | Yoon |
| 4,930,674 A | 6/1990 | Barak |
| 4,968,315 A | 11/1990 | Gatturna |
| 4,976,715 A | 12/1990 | Bays et al. |
| 4,994,073 A | 2/1991 | Green |
| 4,997,436 A | 3/1991 | Oberlander |
| 5,002,563 A | 3/1991 | Pyka et al. |
| 5,013,316 A | 5/1991 | Goble et al. |
| 5,015,249 A | 5/1991 | Nakao et al. |
| 5,037,422 A | 8/1991 | Hayhurst et al. |
| 5,041,129 A | 8/1991 | Hayhurst et al. |
| 5,046,513 A | 9/1991 | Gatturna et al. |
| 5,053,047 A | 10/1991 | Yoon |
| 5,059,206 A | 10/1991 | Winters |
| 5,062,563 A | 11/1991 | Green et al. |
| 5,100,417 A | 3/1992 | Cerier et al. |
| 5,102,421 A | 4/1992 | Anspach, Jr. |
| 5,116,357 A | 5/1992 | Eberbach |
| 5,122,155 A | 6/1992 | Eberbach |
| 5,123,913 A | 6/1992 | Wilk et al. |

(56) References Cited

U.S. PATENT DOCUMENTS

| | | | |
|---|---|---|---|
| RE34,021 E | 8/1992 | Mueller et al. |
| 5,141,515 A | 8/1992 | Eberbach |
| 5,141,520 A | 8/1992 | Goble et al. |
| 5,156,609 A | 10/1992 | Nakao et al. |
| 5,156,616 A | 10/1992 | Meadows et al. |
| 5,167,665 A | 12/1992 | McKinney |
| 5,171,259 A | 12/1992 | Inoue |
| 5,174,295 A | 12/1992 | Christian et al. |
| 5,174,487 A | 12/1992 | Rothfuss et al. |
| 5,176,682 A | 1/1993 | Chow |
| 5,176,692 A | 1/1993 | Wilk et al. |
| 5,203,787 A | 4/1993 | Noblitt et al. |
| 5,217,472 A | 6/1993 | Green et al. |
| 5,224,946 A | 7/1993 | Hayhurst et al. |
| 5,242,457 A | 9/1993 | Akopov et al. |
| 5,246,441 A | 9/1993 | Ross et al. |
| 5,251,642 A | 10/1993 | Handlos |
| 5,261,914 A | 11/1993 | Warren |
| 5,269,753 A | 12/1993 | Wilk |
| 5,269,783 A | 12/1993 | Sander |
| 5,282,829 A | 2/1994 | Hermes |
| 5,289,963 A | 3/1994 | McGarry et al. |
| 5,290,217 A | 3/1994 | Campos |
| 5,304,187 A | 4/1994 | Green |
| 5,333,624 A | 8/1994 | Tovey |
| 5,342,396 A | 8/1994 | Cook |
| 5,350,400 A | 9/1994 | Esposito et al. |
| 5,352,229 A | 10/1994 | Goble et al. |
| 5,354,292 A | 10/1994 | Braeuer et al. |
| 5,364,408 A | 11/1994 | Gordon |
| 5,366,460 A | 11/1994 | Eberbach |
| 5,370,650 A | 12/1994 | Tovey et al. |
| 5,372,604 A | 12/1994 | Trott |
| 5,380,334 A | 1/1995 | Torrie et al. |
| 5,383,477 A | 1/1995 | Dematteis |
| 5,395,383 A * | 3/1995 | Adams ............... A61F 2/0063 606/198 |
| 5,397,332 A | 3/1995 | Kammerer et al. |
| 5,403,326 A | 4/1995 | Harrison |
| 5,405,360 A * | 4/1995 | Tovey ............... A61F 2/0063 606/151 |
| 5,411,522 A | 5/1995 | Trott |
| 5,411,523 A | 5/1995 | Goble |
| 5,417,691 A | 5/1995 | Hayhurst |
| 5,417,712 A | 5/1995 | Whittaker et al. |
| 5,425,490 A | 6/1995 | Goble et al. |
| 5,441,502 A | 8/1995 | Bartlett |
| 5,441,508 A | 8/1995 | Gazielly et al. |
| 5,456,720 A | 10/1995 | Schultz et al. |
| 5,464,403 A | 11/1995 | Kieturakis et al. |
| 5,478,354 A | 12/1995 | Tovey et al. |
| 5,486,197 A | 1/1996 | Le et al. |
| 5,497,933 A | 3/1996 | Defonzo et al. |
| 5,500,000 A | 3/1996 | Feagin et al. |
| 5,501,695 A | 3/1996 | Anspach, Jr. et al. |
| 5,503,623 A | 4/1996 | Tilton, Jr. |
| 5,505,735 A | 4/1996 | Li |
| 5,507,754 A | 4/1996 | Green et al. |
| 5,520,700 A | 5/1996 | Beyar et al. |
| 5,522,817 A | 6/1996 | Sander et al. |
| 5,545,180 A | 8/1996 | Le et al. |
| 5,560,532 A | 10/1996 | DeFonzo et al. |
| 5,562,689 A | 10/1996 | Green et al. |
| 5,569,306 A | 10/1996 | Thal |
| 5,582,616 A | 12/1996 | Bolduc et al. |
| 5,584,835 A | 12/1996 | Greenfield |
| 5,618,314 A | 4/1997 | Harwin et al. |
| 5,622,257 A | 4/1997 | Deschenes et al. |
| 5,628,751 A | 5/1997 | Sander et al. |
| 5,643,319 A | 7/1997 | Green et al. |
| 5,643,321 A | 7/1997 | McDevitt |
| 5,647,874 A | 7/1997 | Hayhurst |
| 5,649,963 A | 7/1997 | McDevitt |
| 5,662,683 A | 9/1997 | Kay |
| 5,667,513 A | 9/1997 | Torrie et al. |
| 5,674,245 A | 10/1997 | Ilgen |
| 5,681,342 A | 10/1997 | Benchetrit |
| 5,702,215 A | 12/1997 | Li |
| 5,713,903 A | 2/1998 | Sanders et al. |
| 5,720,753 A | 2/1998 | Sander et al. |
| 5,725,541 A | 3/1998 | Anspach, III et al. |
| 5,741,282 A | 4/1998 | Anspach, III et al. |
| 5,766,246 A | 6/1998 | Mulhauser et al. |
| 5,782,864 A | 7/1998 | Lizardi |
| 5,797,909 A | 8/1998 | Michelson |
| 5,797,931 A | 8/1998 | Bito et al. |
| 5,797,963 A | 8/1998 | McDevitt |
| 5,807,403 A | 9/1998 | Beyar et al. |
| 5,830,221 A | 11/1998 | Stein et al. |
| 5,836,961 A | 11/1998 | Kieturakis et al. |
| 5,868,762 A | 2/1999 | Cragg et al. |
| 5,873,891 A | 2/1999 | Sohn |
| 5,885,258 A | 3/1999 | Sachdeva et al. |
| 5,885,294 A | 3/1999 | Pedlick et al. |
| 5,893,856 A | 4/1999 | Jacob et al. |
| 5,904,696 A | 5/1999 | Rosenman |
| 5,919,184 A | 7/1999 | Tilton, Jr. |
| 5,922,026 A | 7/1999 | Chin |
| 5,928,244 A | 7/1999 | Tovey et al. |
| 5,948,000 A | 9/1999 | Larsen et al. |
| 5,957,939 A | 9/1999 | Heaven et al. |
| 5,957,953 A | 9/1999 | Dipoto et al. |
| 5,968,044 A | 10/1999 | Nicholson et al. |
| 5,980,557 A | 11/1999 | Iserin et al. |
| 5,989,265 A | 11/1999 | Bouquet De La Joliniere et al. |
| 5,997,552 A | 12/1999 | Person et al. |
| 6,063,088 A | 5/2000 | Winslow |
| 6,156,045 A | 12/2000 | Ulbrich et al. |
| 6,179,840 B1 | 1/2001 | Bowman |
| 6,193,731 B1 | 2/2001 | Oppelt et al. |
| 6,193,733 B1 | 2/2001 | Adams |
| 6,245,072 B1 | 6/2001 | Zdeblick et al. |
| 6,302,885 B1 | 10/2001 | Essiger |
| 6,312,442 B1 | 11/2001 | Kieturakis et al. |
| 6,315,789 B1 | 11/2001 | Cragg |
| 6,318,616 B1 | 11/2001 | Pasqualucci et al. |
| 6,322,563 B1 | 11/2001 | Cummings et al. |
| 6,325,805 B1 | 12/2001 | Ogilvie et al. |
| 6,387,113 B1 | 5/2002 | Hawkins et al. |
| 6,391,333 B1 | 5/2002 | Li et al. |
| 6,397,332 B2 | 5/2002 | Kawano et al. |
| 6,413,274 B1 | 7/2002 | Pedros |
| 6,425,900 B1 | 7/2002 | Knodel et al. |
| 6,436,110 B2 | 8/2002 | Bowman et al. |
| 6,447,522 B2 | 9/2002 | Gambale et al. |
| 6,447,524 B1 | 9/2002 | Knodel et al. |
| 6,478,803 B1 | 11/2002 | Kapec et al. |
| 6,482,178 B1 | 11/2002 | Andrews et al. |
| 6,482,210 B1 | 11/2002 | Skiba et al. |
| 6,506,190 B1 | 1/2003 | Walshe |
| 6,511,499 B2 | 1/2003 | Schmieding et al. |
| 6,517,564 B1 | 2/2003 | Grafton et al. |
| 6,524,316 B1 | 2/2003 | Nicholson et al. |
| 6,527,795 B1 | 3/2003 | Lizardi |
| 6,530,933 B1 | 3/2003 | Yeung et al. |
| 6,540,769 B1 | 4/2003 | Miller, III |
| 6,551,333 B2 | 4/2003 | Kuhns et al. |
| 6,554,852 B1 | 4/2003 | Oberlander |
| 6,569,186 B1 | 5/2003 | Winters et al. |
| 6,575,976 B2 | 6/2003 | Grafton |
| 6,599,289 B1 | 7/2003 | Bojarski et al. |
| 6,620,185 B1 | 9/2003 | Harvie et al. |
| 6,629,988 B2 | 10/2003 | Weadock |
| 6,638,297 B1 | 10/2003 | Huitema |
| 6,648,893 B2 | 11/2003 | Dudasik |
| 6,666,872 B2 | 12/2003 | Barreiro et al. |
| 6,673,094 B1 | 1/2004 | McDevitt et al. |
| 6,685,728 B2 | 2/2004 | Sinnott et al. |
| 6,692,506 B1 | 2/2004 | Ory et al. |
| 6,723,099 B1 | 4/2004 | Goshert |
| 6,726,704 B1 | 4/2004 | Loshakove et al. |
| 6,726,705 B2 | 4/2004 | Peterson et al. |
| 6,740,100 B2 | 5/2004 | Demopulos et al. |
| 6,746,472 B2 | 6/2004 | Frazier et al. |

(56) References Cited

U.S. PATENT DOCUMENTS

| | | |
|---|---|---|
| 6,764,500 B1 | 7/2004 | Muijs Van De Moer et al. |
| 6,770,073 B2 | 8/2004 | McDevitt et al. |
| 6,779,701 B2 | 8/2004 | Bailly et al. |
| 6,800,081 B2 | 10/2004 | Parodi |
| 6,835,206 B2 | 12/2004 | Jackson |
| 6,849,078 B2 | 2/2005 | Durgin et al. |
| 6,887,259 B2 | 5/2005 | Lizardi |
| 6,926,723 B1 | 5/2005 | Mulhauser et al. |
| 6,932,834 B2 | 5/2005 | Lizardi et al. |
| 6,939,365 B1 | 9/2005 | Fogarty et al. |
| 6,946,003 B1 | 9/2005 | Wolowacz et al. |
| 6,949,117 B2 | 9/2005 | Gambale et al. |
| 6,964,685 B2 | 11/2005 | Murray et al. |
| 6,966,916 B2 | 11/2005 | Kumar |
| 6,972,027 B2 | 12/2005 | Fallin et al. |
| 6,984,241 B2 | 1/2006 | Lubbers et al. |
| 6,991,597 B2 | 1/2006 | Gellman et al. |
| 7,008,435 B2 | 3/2006 | Cummins |
| 7,021,316 B2 | 4/2006 | Leiboff |
| 7,025,772 B2 | 4/2006 | Gellman et al. |
| 7,033,379 B2 | 4/2006 | Peterson |
| 7,037,324 B2 | 5/2006 | Martinek |
| 7,048,171 B2 | 5/2006 | Thornton et al. |
| 7,063,711 B1 | 6/2006 | Loshakove et al. |
| 7,083,638 B2 | 8/2006 | Foerster |
| 7,087,064 B1 | 8/2006 | Hyde |
| 7,112,214 B2 | 9/2006 | Peterson et al. |
| 7,118,581 B2 | 10/2006 | Fridén |
| 7,144,413 B2 | 12/2006 | Wilford et al. |
| 7,144,414 B2 | 12/2006 | Harvie et al. |
| 7,150,750 B2 | 12/2006 | Demarati |
| 7,153,314 B2 | 12/2006 | Laufer et al. |
| 7,160,314 B2 | 1/2007 | Sgro et al. |
| 7,160,326 B2 | 1/2007 | Ball |
| 7,163,551 B2 | 1/2007 | Anthony et al. |
| 7,163,563 B2 | 1/2007 | Schwartz et al. |
| 7,169,157 B2 | 1/2007 | Kayan |
| 7,189,251 B2 | 3/2007 | Kay |
| 7,201,754 B2 | 4/2007 | Stewart et al. |
| 7,214,232 B2 | 5/2007 | Bowman et al. |
| 7,226,469 B2 | 6/2007 | Benavitz et al. |
| 7,229,452 B2 | 6/2007 | Kayan |
| 7,247,164 B1 | 7/2007 | Ritchart et al. |
| 7,303,577 B1 | 12/2007 | Dean |
| 7,309,337 B2 | 12/2007 | Colleran et al. |
| 7,320,692 B1 | 1/2008 | Bender et al. |
| 7,320,701 B2 | 1/2008 | Haut et al. |
| 7,322,935 B2 | 1/2008 | Palmer et al. |
| 7,326,231 B2 | 2/2008 | Phillips et al. |
| 7,343,920 B2 | 3/2008 | Toby et al. |
| 7,368,124 B2 | 5/2008 | Chun et al. |
| 7,377,934 B2 | 5/2008 | Lin et al. |
| 7,381,213 B2 | 6/2008 | Lizardi |
| 7,390,329 B2 | 6/2008 | Westra et al. |
| 7,399,304 B2 | 7/2008 | Gambale et al. |
| 7,404,824 B1 | 7/2008 | Webler et al. |
| 7,416,554 B2 | 8/2008 | Lam et al. |
| 7,452,368 B2 | 11/2008 | Liberatore et al. |
| 7,460,913 B2 | 12/2008 | Kuzma et al. |
| 7,463,933 B2 | 12/2008 | Wahlstron et al. |
| 7,465,308 B2 | 12/2008 | Sikora et al. |
| 7,481,832 B1 | 1/2009 | Miridew et al. |
| 7,485,124 B2 | 2/2009 | Kuhns et al. |
| 7,497,854 B2 | 3/2009 | Gill et al. |
| 7,500,972 B2 | 3/2009 | Voegele et al. |
| 7,500,980 B2 | 3/2009 | Gill et al. |
| 7,500,983 B1 | 3/2009 | Kaiser et al. |
| 7,503,474 B2 | 3/2009 | Hillstead et al. |
| 7,506,791 B2 | 3/2009 | Omaits et al. |
| 7,559,941 B2 | 7/2009 | Zannis et al. |
| 7,572,276 B2 | 8/2009 | Lim et al. |
| 7,585,311 B2 | 9/2009 | Green et al. |
| 7,766,208 B2 | 8/2010 | Epperly et al. |
| 7,771,440 B2 | 8/2010 | Ortiz et al. |
| 7,776,057 B2 | 8/2010 | Laufer et al. |
| 7,780,685 B2 | 8/2010 | Hunt et al. |
| 7,785,255 B2 | 8/2010 | Malkani |
| 7,807,192 B2 | 10/2010 | Li et al. |
| 7,819,880 B2 | 10/2010 | Zannis et al. |
| 7,918,879 B2 | 4/2011 | Yeung et al. |
| 8,114,101 B2 | 2/2012 | Criscuolo et al. |
| 8,197,837 B2 | 6/2012 | Jamiolkowski et al. |
| 9,033,201 B2 | 5/2015 | Euteneuer |
| 9,101,460 B2 | 8/2015 | Euteneuer et al. |
| 9,107,661 B2 | 8/2015 | Euteneuer et al. |
| 9,179,961 B2 | 11/2015 | Euteneuer et al. |
| 9,198,751 B2 | 12/2015 | Euteneuer et al. |
| 9,271,726 B2 | 1/2016 | Euteneuer |
| 10,085,785 B2 | 10/2018 | Euteneuer et al. |
| 10,881,441 B2 | 1/2021 | Euteneuer et al. |
| 11,723,706 B2 * | 8/2023 | Euteneuer ......... A61B 17/0642 606/151 |
| 2002/0077687 A1 | 6/2002 | Ahn |
| 2002/0090725 A1 | 7/2002 | Simpson et al. |
| 2002/0123767 A1 | 9/2002 | Prestel |
| 2002/0165559 A1 | 11/2002 | Grant et al. |
| 2003/0073979 A1 | 4/2003 | Naimark et al. |
| 2003/0125748 A1 | 7/2003 | Li et al. |
| 2003/0212456 A1 | 11/2003 | Lipchitz et al. |
| 2004/0059416 A1 | 3/2004 | Murray et al. |
| 2004/0138705 A1 | 7/2004 | Heino et al. |
| 2004/0167519 A1 | 8/2004 | Weiner et al. |
| 2005/0015021 A1 | 1/2005 | Shiber |
| 2005/0049618 A1 | 3/2005 | Masuda et al. |
| 2005/0051597 A1 | 3/2005 | Toledano |
| 2005/0059996 A1 | 3/2005 | Bauman et al. |
| 2005/0060033 A1 | 3/2005 | Vacanti et al. |
| 2005/0107807 A1 | 5/2005 | Nakao |
| 2005/0113736 A1 | 5/2005 | Orr et al. |
| 2005/0171569 A1 | 8/2005 | Girard et al. |
| 2005/0187576 A1 | 8/2005 | Whitman et al. |
| 2005/0240222 A1 | 10/2005 | Shipp |
| 2005/0274768 A1 | 12/2005 | Cummins et al. |
| 2006/0074423 A1 | 4/2006 | Alleyne et al. |
| 2006/0155165 A1 | 7/2006 | Vanden Hoek et al. |
| 2006/0178743 A1 | 8/2006 | Carter |
| 2006/0235442 A1 | 10/2006 | Huitema |
| 2006/0293760 A1 | 12/2006 | DeDeyne |
| 2007/0078477 A1 | 4/2007 | Heneveld, Sr. et al. |
| 2007/0083236 A1 | 4/2007 | Sikora et al. |
| 2007/0112361 A1 | 5/2007 | Schonholz et al. |
| 2007/0179531 A1 | 8/2007 | Thornes |
| 2007/0185506 A1 | 8/2007 | Jackson |
| 2007/0190108 A1 | 8/2007 | Datta et al. |
| 2007/0219558 A1 | 9/2007 | Deutsch |
| 2007/0270804 A1 | 11/2007 | Chudik |
| 2007/0288023 A1 | 12/2007 | Pellegrino et al. |
| 2007/0299299 A1 | 12/2007 | Rosenblatt |
| 2008/0027470 A1 | 1/2008 | Hart et al. |
| 2008/0051888 A1 | 2/2008 | Ratcliffe et al. |
| 2008/0065153 A1 | 3/2008 | Allard et al. |
| 2008/0090936 A1 | 4/2008 | Fujimura et al. |
| 2008/0125869 A1 | 5/2008 | Paz et al. |
| 2008/0135600 A1 | 6/2008 | Hiranuma et al. |
| 2008/0173691 A1 | 7/2008 | Mas et al. |
| 2008/0188874 A1 | 8/2008 | Henderson |
| 2008/0188936 A1 | 8/2008 | Ball et al. |
| 2008/0195119 A1 | 8/2008 | Ferree |
| 2008/0200949 A1 | 8/2008 | Hiles et al. |
| 2008/0241213 A1 | 10/2008 | Chun et al. |
| 2008/0272173 A1 | 11/2008 | Coleman et al. |
| 2008/0306408 A1 | 12/2008 | Lo |
| 2009/0001122 A1 | 1/2009 | Prommersberger et al. |
| 2009/0012521 A1 | 1/2009 | Axelson, Jr. et al. |
| 2009/0030434 A1 | 1/2009 | Paz et al. |
| 2009/0069806 A1 | 3/2009 | De La Mora Levy et al. |
| 2009/0076541 A1 | 3/2009 | Chin et al. |
| 2009/0105535 A1 | 4/2009 | Green et al. |
| 2009/0112085 A1 | 4/2009 | Eby |
| 2009/0134198 A1 | 5/2009 | Knodel et al. |
| 2009/0156986 A1 | 6/2009 | Trenhaile |
| 2009/0156997 A1 | 6/2009 | Trenhaile |
| 2009/0182245 A1 | 7/2009 | Zambelli |
| 2009/0242609 A1 | 10/2009 | Kanner |

(56) References Cited

U.S. PATENT DOCUMENTS

| | | |
|---|---|---|
| 2010/0145367 A1 | 6/2010 | Ratcliffe |
| 2010/0147922 A1 | 6/2010 | Olson |
| 2010/0163598 A1 | 7/2010 | Belzer |
| 2010/0191332 A1 | 7/2010 | Euteneuer et al. |
| 2010/0241227 A1 | 9/2010 | Euteneuer et al. |
| 2010/0249801 A1 | 9/2010 | Sengun et al. |
| 2010/0256675 A1 | 10/2010 | Romans |
| 2010/0274278 A1 | 10/2010 | Fleenor et al. |
| 2010/0292715 A1 | 11/2010 | Nering et al. |
| 2010/0292791 A1 | 11/2010 | Lu et al. |
| 2010/0312250 A1 | 12/2010 | Euteneuer et al. |
| 2010/0312275 A1 | 12/2010 | Euteneuer et al. |
| 2010/0327042 A1 | 12/2010 | Amid et al. |
| 2011/0000950 A1 | 1/2011 | Euteneuer et al. |
| 2011/0011917 A1 | 1/2011 | Loumet |
| 2011/0034942 A1 | 2/2011 | Levin et al. |
| 2011/0040310 A1 | 2/2011 | Levin et al. |
| 2011/0040311 A1 | 2/2011 | Levin et al. |
| 2011/0066166 A1 | 3/2011 | Levin et al. |
| 2011/0106154 A1 | 5/2011 | DeMatteo et al. |
| 2011/0114700 A1 | 5/2011 | Baxter, III et al. |
| 2011/0224702 A1 | 9/2011 | Van Kampen et al. |
| 2011/0264149 A1 | 10/2011 | Pappalardo et al. |
| 2012/0160893 A1 | 6/2012 | Harris et al. |
| 2012/0193391 A1 | 8/2012 | Michler et al. |
| 2012/0209401 A1 | 8/2012 | Euteneuer et al. |
| 2012/0248171 A1 | 10/2012 | Bailly et al. |
| 2012/0316608 A1 | 12/2012 | Foley |
| 2013/0153627 A1 | 6/2013 | Euteneuer et al. |
| 2013/0158587 A1 | 6/2013 | Euteneuer et al. |
| 2013/0172920 A1 | 7/2013 | Euteneuer et al. |
| 2013/0184716 A1 | 7/2013 | Euteneuer et al. |
| 2013/0240598 A1 | 9/2013 | Euteneuer et al. |
| 2013/0245627 A1 | 9/2013 | Euteneuer et al. |
| 2013/0245682 A1 | 9/2013 | Euteneuer et al. |
| 2013/0245683 A1 | 9/2013 | Euteneuer et al. |
| 2013/0245706 A1 | 9/2013 | Euteneuer et al. |
| 2013/0245707 A1 | 9/2013 | Euteneuer et al. |
| 2013/0245762 A1 | 9/2013 | Van Kampen et al. |
| 2013/0245774 A1 | 9/2013 | Euteneuer et al. |

FOREIGN PATENT DOCUMENTS

| | | |
|---|---|---|
| EP | 0298400 A1 | 1/1989 |
| EP | 0390613 A1 | 10/1990 |
| EP | 543499 A1 | 5/1993 |
| EP | 0548998 A1 | 6/1993 |
| EP | 0557963 A1 | 9/1993 |
| EP | 0589306 A2 | 3/1994 |
| EP | 0908152 A1 | 4/1999 |
| EP | 1491157 A1 | 12/2004 |
| EP | 1559379 A1 | 8/2005 |
| EP | 2030576 A2 | 3/2009 |
| GB | 2154688 A | 9/1985 |
| GB | 2397240 A | 7/2004 |
| JP | 58188442 A | 11/1983 |
| JP | 2005506122 A | 3/2005 |
| JP | 2006515774 A | 6/2006 |
| WO | 85005025 | 11/1985 |
| WO | 0176456 A2 | 10/2001 |
| WO | 2002034140 A2 | 5/2002 |
| WO | 2003105670 A2 | 12/2003 |
| WO | 2004000138 A1 | 12/2003 |
| WO | 2004093690 A1 | 11/2004 |
| WO | 2005016389 A2 | 2/2005 |
| WO | 2006086679 A1 | 8/2006 |
| WO | 2007014910 A1 | 2/2007 |
| WO | 2007030676 A2 | 3/2007 |
| WO | 2007078978 A2 | 7/2007 |
| WO | 2007082088 A2 | 7/2007 |
| WO | 2008111073 A2 | 9/2008 |
| WO | 2008111078 A2 | 9/2008 |
| WO | 2008139473 A2 | 11/2008 |
| WO | 2009079211 A1 | 6/2009 |
| WO | 2009143331 A1 | 11/2009 |
| WO | 2011095890 A2 | 8/2011 |
| WO | 2011128903 A2 | 10/2011 |

OTHER PUBLICATIONS

Bahler et al., "Trabecular bypass stents decrease intraocular pressure in cultured himan anterior segments", Am. J. Opthalmology, Dec. 2004, pp. 988-994, vol. 138, No. 6.

Chamay et al., "Digital contracture deformity after implantation of a silicone prosthesis: Light and electron microscopic study", The Journal of Hand Surgery, vol. 3, No. 3, pp. 266-270, May 1978.

D'Ermo et al., "Our results with the operation of ab externo", Ophthalmologica, vol. 168, pp. 347-355, 1971.

France et al., "Biomechanical evaluation of rotator cuff fixation methods", The American Journal of Sports Medicine, vol. 17, No. 2, 1989.

Goodship et al., "An assessment of filamentous carbon fibre for the treatment of tendon injury in the horse", Veterinary Records, pp. 217-221, vol. 106, Mar. 8, 1980.

Hunter et al., "Flexor-tendon reconstruction in severely damaged hands", The Journal of Bone and Joint Surgery (American Volume), pp. 329-358, vol. 53-A, No. 5, Jul. 1971.

Johnstone et al., "Microsurgery of Schlemm's canal and the human aqueous outflow system", Am. J. Opthalmology, pp. 906-917, vol. 76, No. 6, Dec. 1973.

Kowalsky et al., "Evaluation of suture abrasion against rotator cuff tendon and proximal humerus bone", Arthroscopy: The Journal of Arthroscopic and Related Surgery, pp. 329-334, vol. 24, No. 3, Mar. 2008.

Lee et al., "Aqueous-venous and intraocular pressure. Preliminary report of animal studies", Investigative Ophthalmonogy, pp. 59-64, vol. 5, No. 1, Feb. 1966.

Maepea et al., "The pressures in the episcleral veins, Schlemm's canal and the trabecular meshwork in monkeys: Effects of changes in intraocular pressure", Exp. Eye Res., pp. 645-663, vol. 49, 1989.

Nicolle et al., "A silastic tendon prosthesis as an adjunct to flexor tendon grafting: An experimental and clinical evaluation", British Journal of Plastic Surgery, pp. 224-236, vol. 22, issues 3-4, 1969.

Rubin et al., "The use of acellular biologic tissue patches in foot and ankle surgery", Clinics in Podiatric Medicine and Surgery, pp. 533-552, nol. 22, 2005.

Schultz, "Canaloplasty procedure shows promise for open-angle glaucoma in European study", Ocular Surgery News, pp. 34-35, Mar. 1, 2007.

Spiegel et al., "Schlemm's canal implant: A new method to lower intraocular pressure in patients with POAG", Ophthalmic Surgery and Lasers, pp. 492-494, vol. 30, No. 6, Jun. 1999.

Stetson et al., "Arthroscopic treatment of partial rotator cuff tears", Operative Techniques in Sports Medicine, pp. 135-148, vol. 12, issue 2, Apr. 2004.

Valdez et al., "Repair of digital flexor tendon lacerations in the horse, using carbon fiber implants", JAYMA, pp. 427-435, vol. 177, No. 5, Sep. 1, 1980.

Wikipedia the Free Encyclopedia, "Rotator cuff tear", downloaded from <https://en.wikipedia.org/wiki/Rotator_cuff_tear> on Dec. 6, 2012, 14 pages.

* cited by examiner

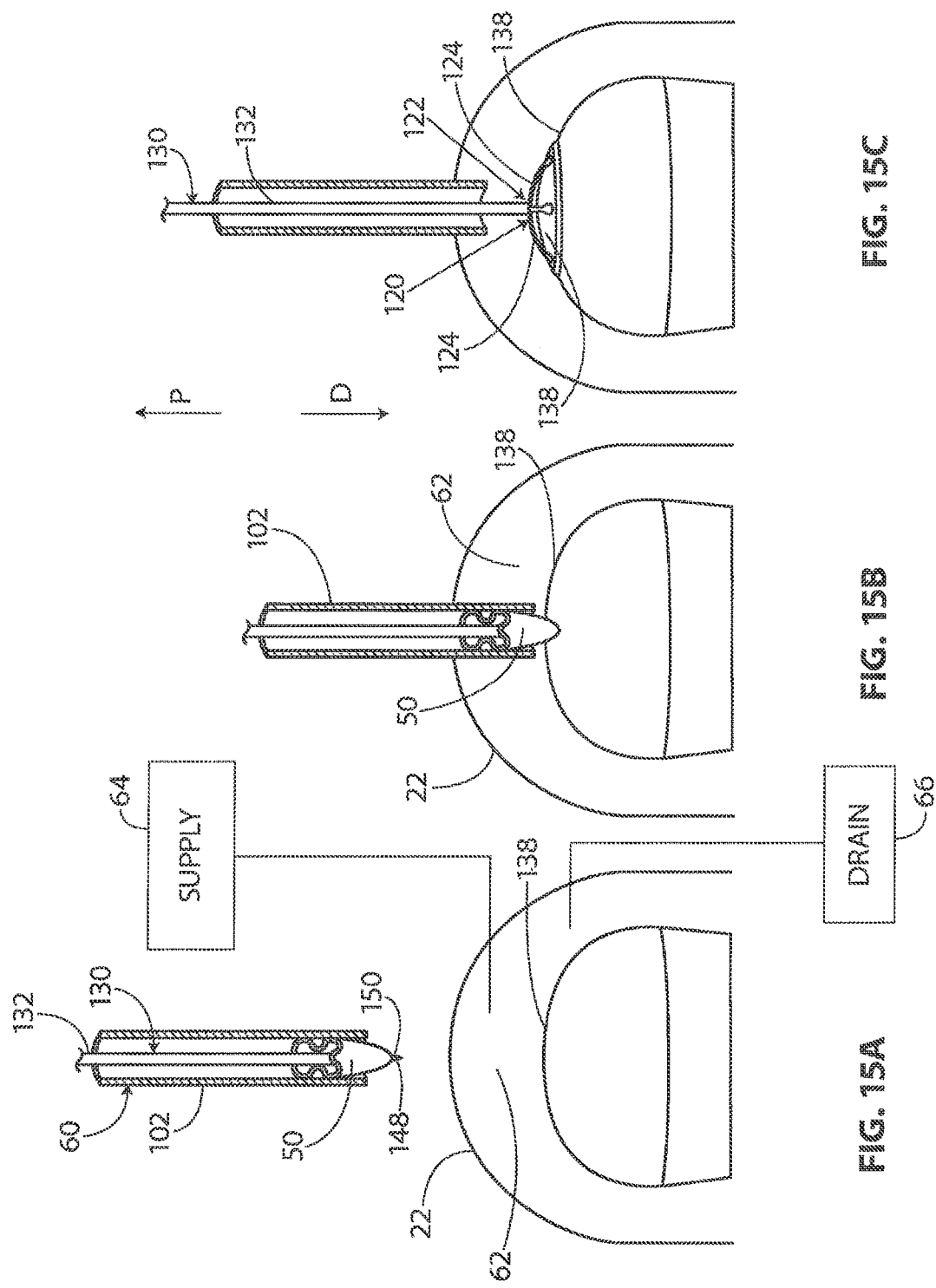

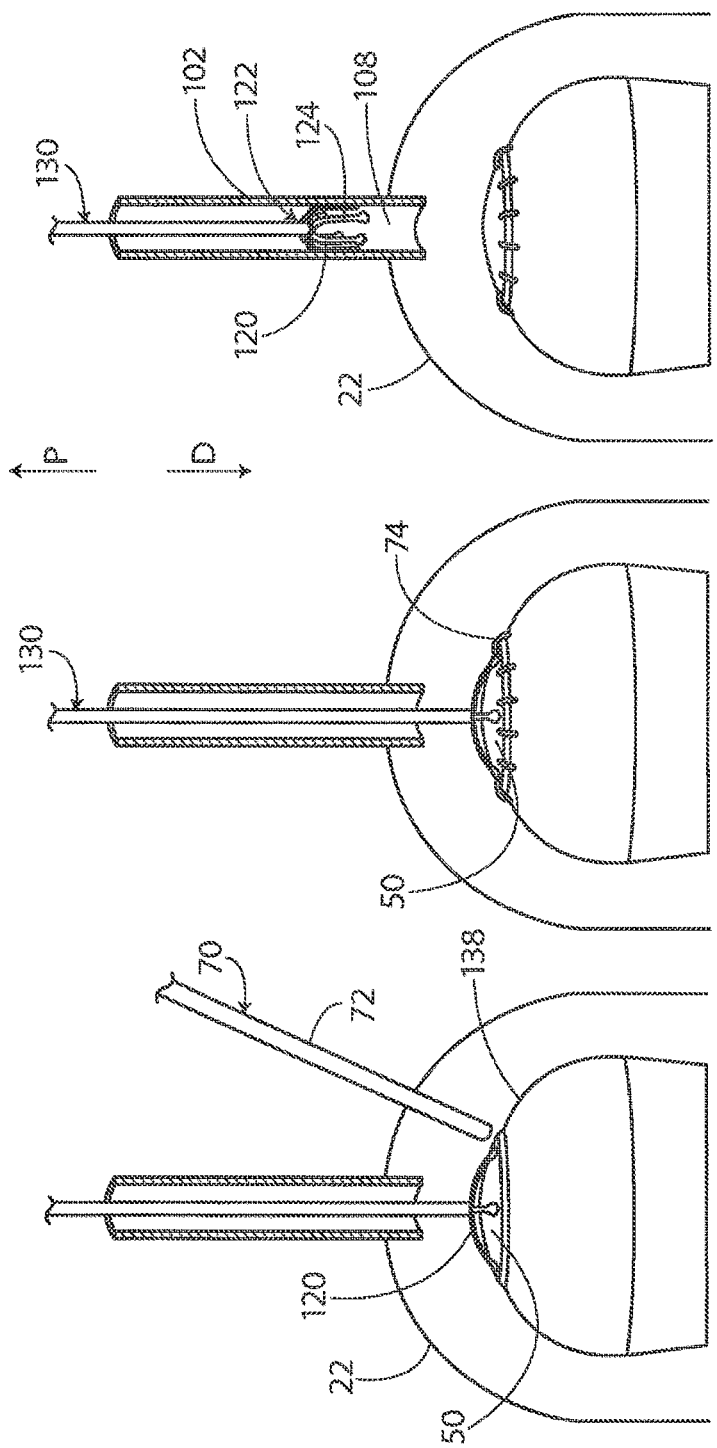

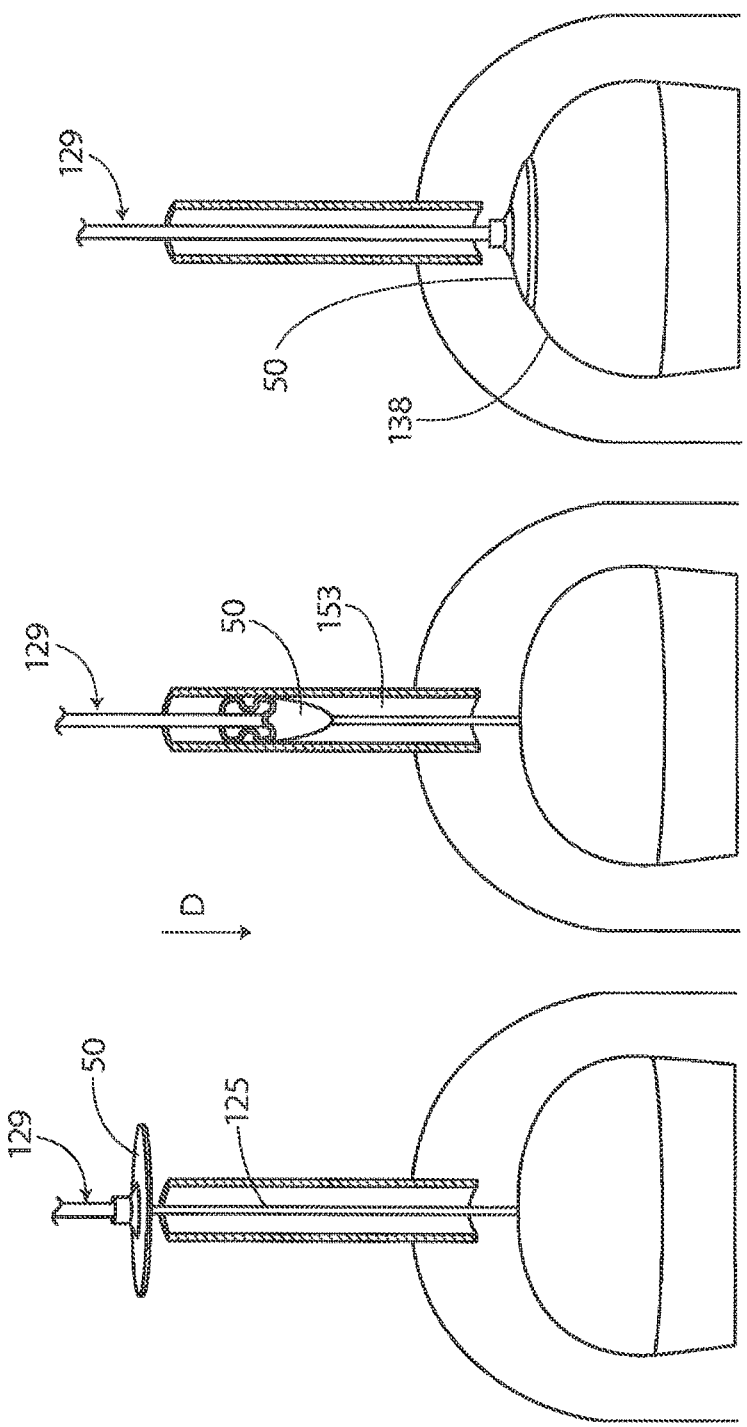

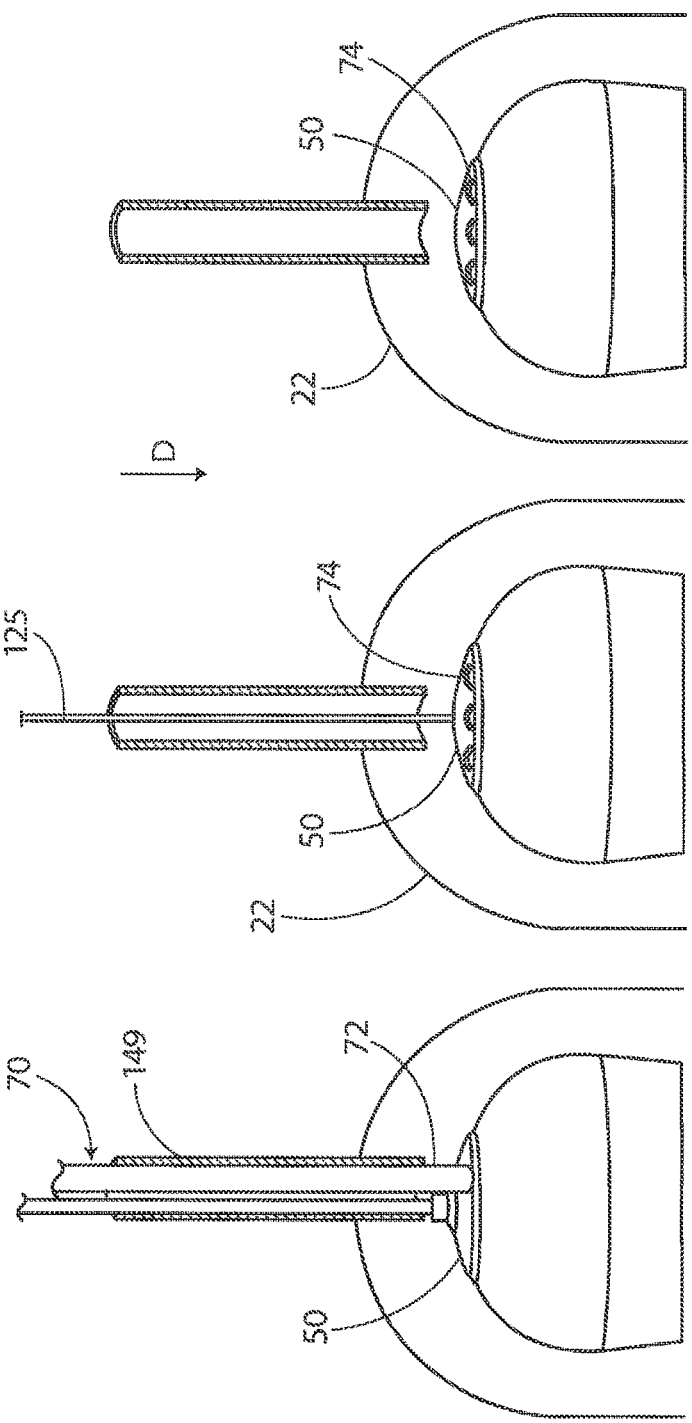

METHODS AND APPARATUS FOR DEPLOYING SHEET-LIKE MATERIALS

CROSS REFERENCE TO RELATED APPLICATIONS

This application is a continuation of U.S. application Ser. No. 17/879,683, filed Aug. 2, 2022, which is a continuation of U.S. application Ser. No. 17/121,258, filed Dec. 14, 2020, which is a continuation of U.S. application Ser. No. 16/136,790 filed on Sep. 20, 2018, which is a continuation of U.S. application Ser. No. 14/883,105 filed on Oct. 14, 2015, which is a continuation of U.S. application Ser. No. 12/794,673 filed on Jun. 4, 2010, which claims benefit to U.S. Provisional Patent Application No. 61/313,116, filed on Mar. 11, 2010 and U.S. Provisional Patent Application No. 61/184,198, filed Jun. 4, 2009. The disclosures of each of which are herein incorporated by reference in their entirety.

INCORPORATION BY REFERENCE

The present application is related to U.S. patent application Ser. No. 12/794,540, U.S. Pat. No. 8,668,718, entitled Methods and Apparatus for Fixing Sheet-like Materials to a Target Tissue, filed on Jun. 4, 2010; U.S. patent application Ser. No. 12/794,551, U.S. Pat. No. 8,821,536, entitled Methods and Apparatus for Delivering Staples to a Target Tissue, filed on Jun. 4, 2010; and, U.S. patent application Ser. No. 12/794,677, U.S. Pat. No. 8,763,878, entitled Methods and Apparatus Having a Bowstring-like Staple Delivery to a Target Tissue, filed on Jun. 4, 2010, the disclosures of each incorporated herein by reference.

All publications and patent applications mentioned in this specification are herein incorporated by reference to the same extent as if each individual publication or patent application was specifically and individually indicated to be incorporated by reference.

FIELD OF THE INVENTION

The present invention relates generally to orthopedic medicine and surgery. More particularly, the present invention relates to methods and apparatus for delivery and fixation of medical devices, such as for treating articulating joints.

BACKGROUND OF THE INVENTION

The glenohumeral joint of the shoulder is found where the head of the humerus mates with a shallow depression in the scapula. This shallow depression is known as the glenoid fossa. Six muscles extend between the humerus and scapula and actuate the glenohumeral joint. These six muscles include the deltoid, the teres major, and the four rotator cuff muscles. As disclosed by Ball et al. in U.S. Patent Publication No. U.S. 2008/0188936 A1 and as illustrated in FIG. 1 the rotator cuff muscles are a complex of four muscles. These four muscles are the supraspinatus, the infraspinatus, the subscapularis, and the teres minor. The centering and stabilizing roles played by the rotator cuff muscles are critical to the proper function of the shoulder. The rotator cuff muscles provide a wide variety of moments to rotate the humerus and to oppose unwanted components of the deltoid and pectoralis muscle forces.

The four muscles of the rotator cuff arise from the scapula 12. The distal tendons of the rotator cuff muscles splay out and interdigitate to form a common continuous insertion on the humerus 14. The subscapularis 16 arises from the anterior aspect of the scapula 12 and attaches over much of the lesser tuberosity of the humerous. The supraspinatus muscle 18 arises from the supraspinatus fossa of the posterior scapula, passes beneath the acromion and the acromioclavicular joint, and attaches to the superior aspect of the greater tuberosity 11. The infraspinatus muscle 13 arises from the infraspinous fossa of the posterior scapula and attaches to the posterolateral aspect of the greater tuberosity 11. The teres minor 15 arises from the lower lateral aspect of the scapula 12 and attaches to the lower aspect of the greater tuberosity 11.

The mechanics of the rotator cuff muscles 10 are complex. The rotator cuff muscles 10 rotate the humerus 14 with respect to the scapula 12, compress the humeral head 17 into the glenoid fossa providing a critical stabilizing mechanism to the shoulder (known as concavity compression), and provide muscular balance. The supraspinatus and infraspinatus provide 45 percent of abduction and 90 percent of external rotation strength. The supraspinatus and deltoid muscles are equally responsible for producing torque about the shoulder joint in the functional planes of motion.

The rotator cuff muscles 10 are critical elements of this shoulder muscle balance equation. The human shoulder has no fixed axis. In a specified position, activation of a muscle creates a unique set of rotational moments. For example, the anterior deltoid can exert moments in forward elevation, internal rotation, and cross-body movement. If forward elevation is to occur without rotation, the cross-body and internal rotation moments of this muscle must be neutralized by other muscles, such as the posterior deltoid and infraspinatus. The timing and magnitude of these balancing muscle effects must be precisely coordinated to avoid unwanted directions of humeral motion. Thus the simplified view of muscles as isolated motors, or as members of force couples must give way to an understanding that all shoulder muscles function together in a precisely coordinated way—opposing muscles canceling out undesired elements leaving only the net torque necessary to produce the desired action. Injury to any of these soft tissues can greatly inhibit ranges and types of motion of the arm.

With its complexity, range of motion and extensive use, a fairly common soft tissue injury is damage to the rotator cuff or rotator cuff tendons. Damage to the rotator cuff is a potentially serious medical condition that may occur during hyperextension, from an acute traumatic tear or from overuse of the joint. With its critical role in abduction, rotational strength and torque production, the most common injury associated with the rotator cuff region is a strain or tear involving the supraspinatus tendon. A tear in the supraspinitus tendon 19 is schematically depicted in FIG. 2. A tear at the insertion site of the tendon with the humerus, may result in the detachment of the tendon from the bone. This detachment may be partial or full, depending upon the severity of the injury. Additionally, the strain or tear can occur within the tendon itself. Injuries to the supraspinatus tendon 19 and recognized modalities for treatment are defined by the type and degree of tear. The first type of tear is a full thickness tear as also depicted in FIG. 2, which as the term indicates is a tear that extends through the thickness of the supraspinatus tendon regardless of whether it is completely torn laterally. The second type of tear is a partial thickness tear which is further classified based on how much of the thickness is torn, whether it is greater or less than 50% of the thickness.

The accepted treatment for a full thickness tear or a partial thickness tear greater than 50% includes reconnecting the torn tendon via sutures. For the partial thickness tears greater than 50%, the tear is completed to a full thickness tear by cutting the tendon prior to reconnection. In contrast to the treatment of a full thickness tear or a partial thickness tear of greater than 50%, the treatment for a partial thickness tear less than 50% usually involves physical cessation from use of the tendon, i.e., rest. Specific exercises can also be prescribed to strengthen and loosen the shoulder area. In many instances, the shoulder does not heal and the partial thickness tear can be the source of chronic pain and stiffness. Further, the pain and stiffness may cause restricted use of the limb which tends to result in further degeneration or atrophy in the shoulder. Surgical intervention may be required for a partial thickness tear of less than 50%, however, current treatment interventions do not include repair of the tendon, rather the surgical procedure is directed to arthroscopic removal of bone to relieve points of impingement or create a larger tunnel between the tendon and bone that is believed to be causing tendon damage. As part of the treatment, degenerated tendon may also be removed using a debridement procedure in which tendon material is ablated. Again, the tendon partial tear is not repaired. Several authors have reported satisfactory early post operative results from these procedures, but over time recurrent symptoms have been noted. In the event of recurrent symptoms, many times a patient will "live with the pain". This may result in less use of the arm and shoulder which further causes degeneration of the tendon and may lead to more extensive damage. A tendon repair would then need to be done in a later procedure if the prescribed treatment for partial tear was unsuccessful in relieving pain and stiffness or over time the tear propagated through injury or degeneration to a full thickness tear or a partial thickness tear greater than 50% with attendant pain and debilitation. A subsequent later procedure would include the more drastic procedure of completing the tear to full thickness and suturing the ends of the tendon back together. This procedure requires extensive rehabilitation, has relatively high failure rates and subjects the patient who first presented and was treated with a partial thickness tear less than 50% to a second surgical procedure.

As described above, adequate treatments do not currently exist for repairing a partial thickness tear of less than 50% in the supraspinatus tendon. Current procedures attempt to alleviate impingement or make room for movement of the tendon to prevent further damage and relieve discomfort but do not repair or strengthen the tendon. Use of the still damaged tendon can lead to further damage or injury. Prior damage may result in degeneration that requires a second more drastic procedure to repair the tendon. Further, if the prior procedure was only partially successful in relieving pain and discomfort, a response may be to use the shoulder less which leads to degeneration and increased likelihood of further injury along with the need for more drastic surgery. There is a large need for surgical techniques and systems to treat partial thickness tears of less than 50% and prevent future tendon damage by strengthening or repairing the native tendon having the partial thickness tear.

SUMMARY OF THE INVENTION

According to aspects of the invention, implant delivery systems for delivering sheet-like implants are disclosed. In some embodiments, the implant delivery system includes a delivery shaft, an implant expander, a sheath, and a sheet-like implant. In these embodiments, the delivery shaft has a proximal end and a distal end. The implant expander is mounted to the distal end of the delivery shaft. The implant expander includes a central portion and a plurality of leg portions radiating from the central portion. The implant expander is evertable between an unstressed configuration in which a distal surface of the implant expander defines a concave surface, and a first compact configuration in which the distal surface of the implant expander defines a convex surface. The implant expander has a first lateral extent when the implant expander is free to assume the unstressed configuration. The sheath defines a lumen having a lumen diameter. At least a portion of the delivery shaft is slidably disposed in the lumen. The lumen diameter is smaller than the first lateral extent of the implant expander so that the sheath holds the implant expander in the first compact configuration when slidably disposed therein. The sheet-like implant overlays at least a portion of the distal surface of the implant expander with portions of the sheet-like implant extending between the leg portions of the implant expander and the sheath.

In some embodiments, a free end of each leg portion of the implant expander is disposed distally of the central portion when the implant expander is assuming the unstressed configuration. The free end of each leg portion is disposed proximally of the central portion when the implant expander is assuming the first compact configuration. The delivery shaft distal end may be fixed to the central portion of the implant expander to urge relative movement between the implant expander and the sheath such that the implant expander and the sheet-like implant can be advanced through a distal opening defined by the sheath so the implant expander is free to assume a deployed configuration.

In some embodiments, a projection extends distally from the distal surface of the central portion of the implant expander to hold the position of delivery system when the projection is held against a target tissue. The implant expander may generally conform to the surface of a target tissue when the implant expander assumes the deployed configuration. In some embodiments, the distal surface of the implant expander defines a concave surface when the implant expander is assuming the deployed configuration and the target tissue has a generally convex shape. A free end of each leg portion may be disposed distally of the central portion when the implant expander is assuming the deployed configuration and the target tissue has a generally convex shape. In some embodiments, the implant expander causes the sheet-like implant to conform to the surface of a target tissue when the implant expander assumes the deployed configuration.

In some embodiments, the implant expander assumes a second compact configuration when the implant expander is retracted proximally into the lumen of the sheath after having assumed the deployed configuration. The distal surface of the implant expander may define a concave surface when the implant expander is assuming the second compact configuration. In some embodiments, the free end of each leg portion is disposed distally of the central portion when the implant expander is assuming the second compact configuration.

In some embodiments, the implant expander is integrally formed of a single material. The sheet-like implant may define a plurality of pockets. Each pocket may be dimensioned to receive a distal portion of a leg portion of the implant expander. In some of these embodiments, the sheet-like implant can be selectively separated from the implant expander by withdrawing the distal portions of the legs from the pockets. In some embodiments, the implant expander further includes a plurality of retainers to engage the sheet-like implant such that the sheet-like implant moves when the implant expander is moved. In some of these embodiments, the sheet-like implant can be selectively separated from the implant expander by withdrawing the retainers from the sheet-like implant.

According to aspects of the present invention, methods of treating a rotator cuff of a shoulder are disclosed. In some embodiments, the method includes the steps of providing an implant delivery system, inflating the shoulder to create a cavity therein, placing the sheet-like implant and the implant expander inside the cavity, allowing the implant expander to assume a deployed configuration, attaching the sheet-like implant to the tendon, urging the implant expander to assume a second compact configuration, and removing the implant expander from the cavity. In these embodiments, the implant delivery system that is provided includes an implant expander. The implant expander has a central portion and a plurality of leg portions radiating from the central portion. The implant expander is evertable between an unstressed configuration in which a distal surface of the implant expander defines a concave surface, and a first compact configuration in which the distal surface of the implant expander defines a convex surface. A sheet-like implant overlays at least a portion of the distal surface of the implant expander. A sheath is disposed about the sheet-like implant and the implant expander. The sheath holds the implant expander in the first compact configuration. When the sheet-like implant and the implant expander are placed inside the cavity, a tendon is contacted with at least a portion of the implant while the implant expander is assuming the first compact configuration. When allowing the implant expander to assume a deployed configuration, the implant expander urges the sheet-like implant against a surface of the tendon. When urging the implant expander to assume a second compact configuration, the distal surface of the implant expander defines a concave surface.

In some embodiments, the implant expander includes a projection extending distally from its central portion. The projection holds the position of the delivery system relative to the tendon when the sheet-like implant and implant expander are placed in the cavity against the tendon.

In some embodiments, the step of allowing the implant expander to assume the deployed configuration includes urging relative movement between the implant expander and the sheath such that the implant expander and the sheet-like implant are advanced through a distal opening defined by the sheath. With this arrangement, the implant expander is free to assume the deployed configuration. In some embodiments, urging relative movement between the implant expander and the sheath includes withdrawing the sheath in a proximal direction relative to the implant expander. In some embodiments, urging relative movement between the implant expander and the sheath includes advancing the implant expander in a distal direction along the lumen of the sheath. In some embodiments, urging the implant expander to assume the second compact configuration includes advancing the sheath over the implant expander so that the implant expander is disposed inside the lumen defined by the sheath. In some embodiments, urging the implant expander to assume the second compact configuration includes drawing the implant expander proximally into the lumen defined by the sheath. In some embodiments, urging the implant expander to assume the second compact configuration includes drawing the implant expander and the projection that extends distally from the central portion of the implant expander proximally into the lumen defined by the sheath.

According to aspects of the invention, methods of preparing a delivery system are disclosed. In some embodiments, these methods include the steps of providing a delivery sheath and an implant expander, covering at least a portion of the distal surface with a sheet-like implant, and deflecting the implant expander. The sheath defines a lumen having a lumen diameter. The implant expander includes a central portion and a plurality of leg portions radiating from the central portion. The implant expander is evertable between an unstressed configuration in which a distal surface of the implant expander defines a concave surface, and a first compact configuration in which the distal surface of the implant expander defines a convex surface. The implant expander has a first lateral extent when the implant expander is free to assume the unstressed configuration. The first lateral extent is greater than the lumen diameter of the sheath. When the implant expander is deflected, the implant expander assumes the first compact configuration and the implant expander and the sheet-like implant are placed in the lumen defined by the sheath. The sheath holds the implant expander in the first compact configuration with portions of the sheet-like implant being interposed between the leg portions of the implant expander and an inner surface of the sheath.

Further aspects of the present invention will become apparent upon review of the Detailed Description with reference to the following drawings.

BRIEF DESCRIPTION OF THE DRAWINGS

FIG. 15A through FIG. 15F are a series of stylized plan views illustrating exemplary methods and apparatus in accordance with the present detailed description.

FIG. 18A through FIG. 18I are a series of stylized plan views illustrating exemplary methods and apparatus in accordance with the present detailed description.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 1:
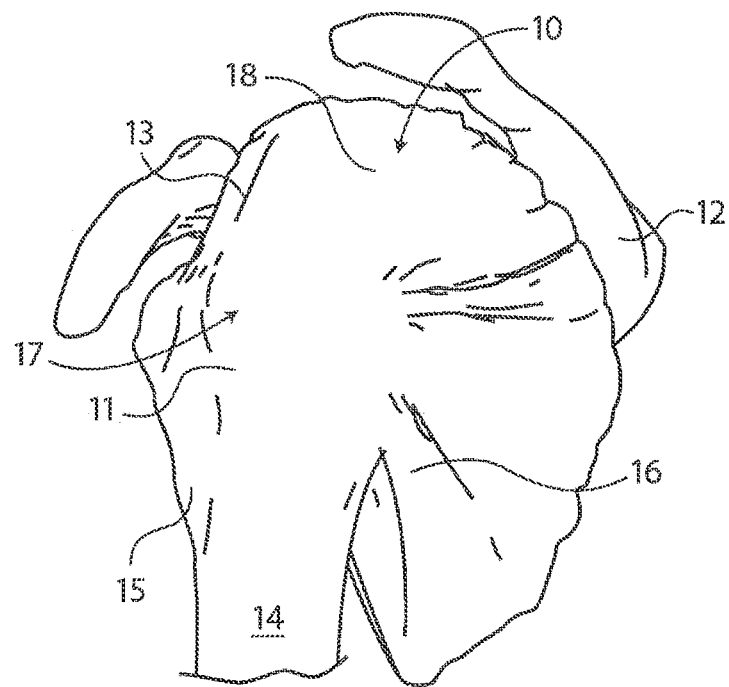
FIG. 1 is a simplified perspective view of the human rotator cuff and associated anatomical structure.
Figure 2:
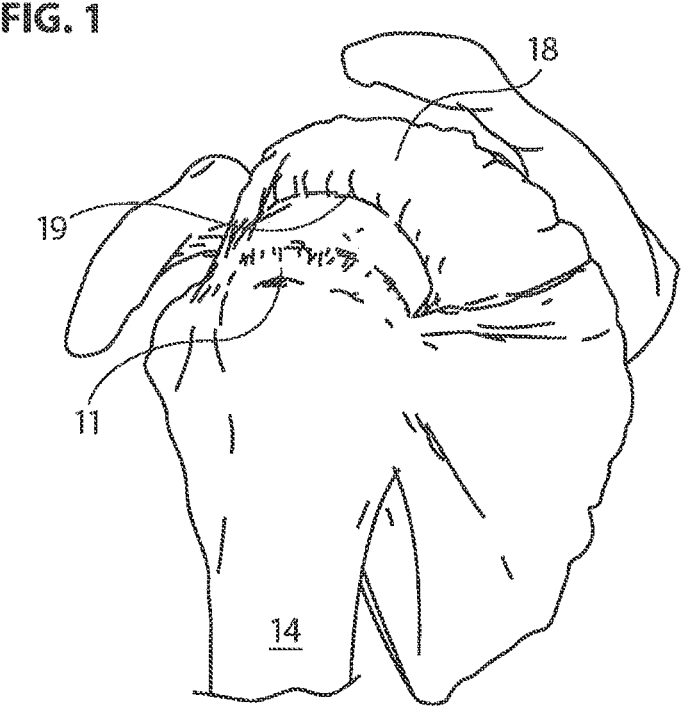
FIG. 2 is a schematic depiction of a full thickness tear in the supraspinatus tendon of the rotator cuff of FIG. 1.
Figure 3:
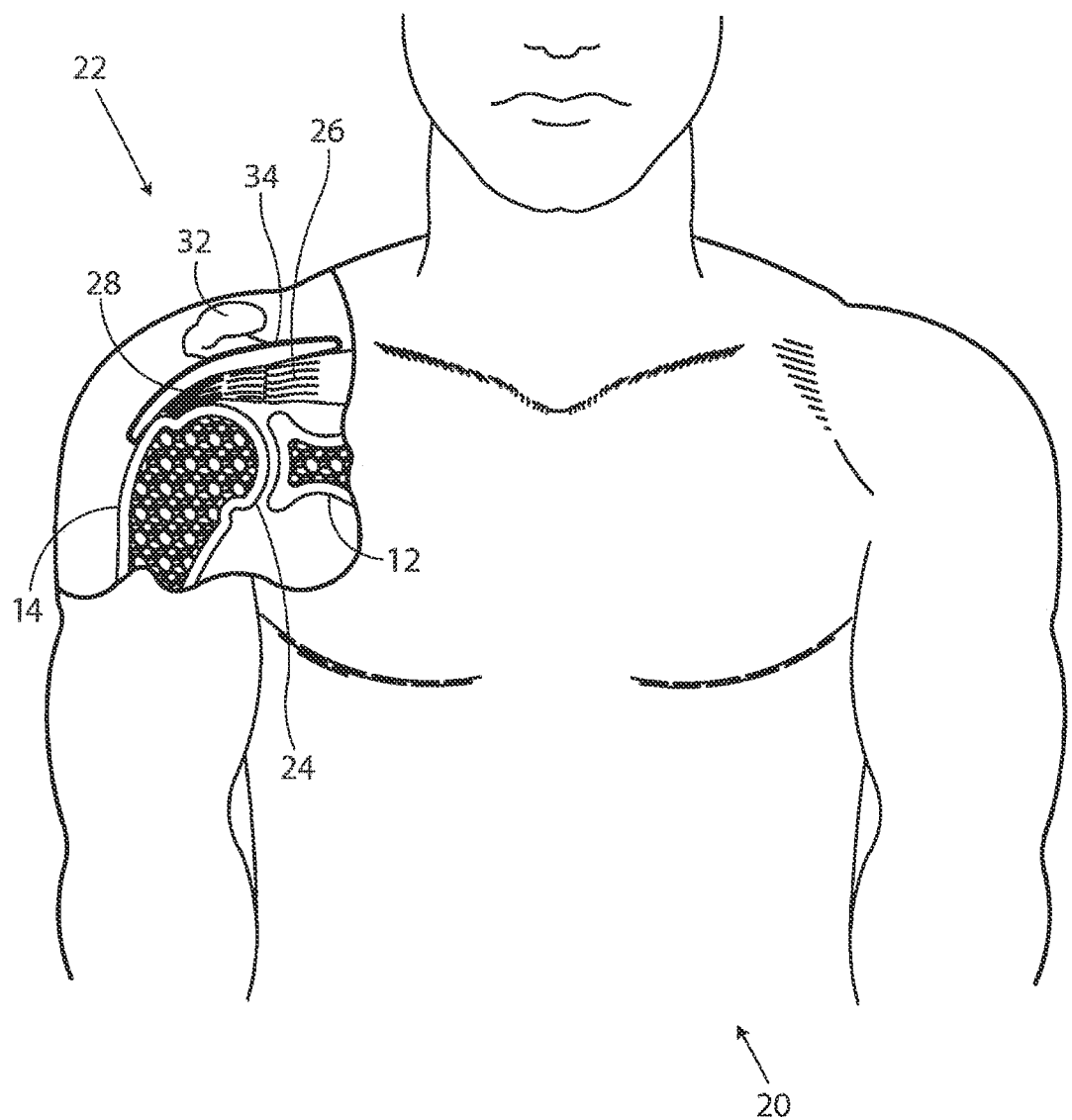
FIG. 3 is a stylized anterior view of a patient with a shoulder being shown in cross-section for purposes of illustration.

FIG. 3 is a stylized anterior view of a patient 20. For purposes of illustration, a shoulder 22 of patient 20 is shown in cross-section in FIG. 3. Shoulder 22 includes a humerus 14 and a scapula 12. In FIG. 3, a head 24 of humerus 14 can be seen mating with a glenoid fossa of scapula 12 at a glenohumeral joint. With reference to FIG. 3, it will be appreciated that the glenoid fossa comprises a shallow depression in scapula 12. The movement of humerus 14 relative to scapula 12 is controlled by a number of muscles including: the deltoid, the supraspinatus, the infraspinatus, the subscapularis, and the teres minor. For purposes of illustration, only the supraspinatus 26 is shown in FIG. 3.

With reference to FIG. 3, it will be appreciated that a distal tendon 28 of the supraspinatus 26 meets humerus 14 at an insertion point. Scapula 12 of shoulder 22 includes an acromium 32. In FIG. 3, a subacromial bursa 34 is shown extending between acromium 32 of scapula 12 and head 24 of humerus 14. In FIG. 3, subacromial bursa 34 is shown overlaying supraspinatus 26. Subacromial bursa 34 is one of the hundreds of bursae found the human body. Each bursa comprises a fluid filled sac. The presence of these bursae in the body reduces friction between bodily tissues. Injury and/or infection of the bursa can cause it to become inflamed. This condition is sometimes referred to as bursitis.

The exemplary methods and apparatus described herein may be used to fix tendon repair implants to various target tissues. For example, a tendon repair implant may be fixed to one or more tendons associated with an articulating joint, such as the glenohumeral joint. The tendons to be treated may be torn, partially torn, have internal micro-tears, be untorn, and/or be thinned due to age, injury or overuse. Applicants believe that the methods and apparatus of the present application and related devices may provide very beneficial therapeutic effect on a patient experiencing joint pain believed to be caused by partial thickness tears and/or internal microtears. By applying a tendon repair implant early before a full tear or other injury develops, the implant may cause the tendon to thicken and/or at least partially repair itself, thereby avoiding more extensive joint damage, pain, and the need for more extensive joint repair surgery.

Figure 4:
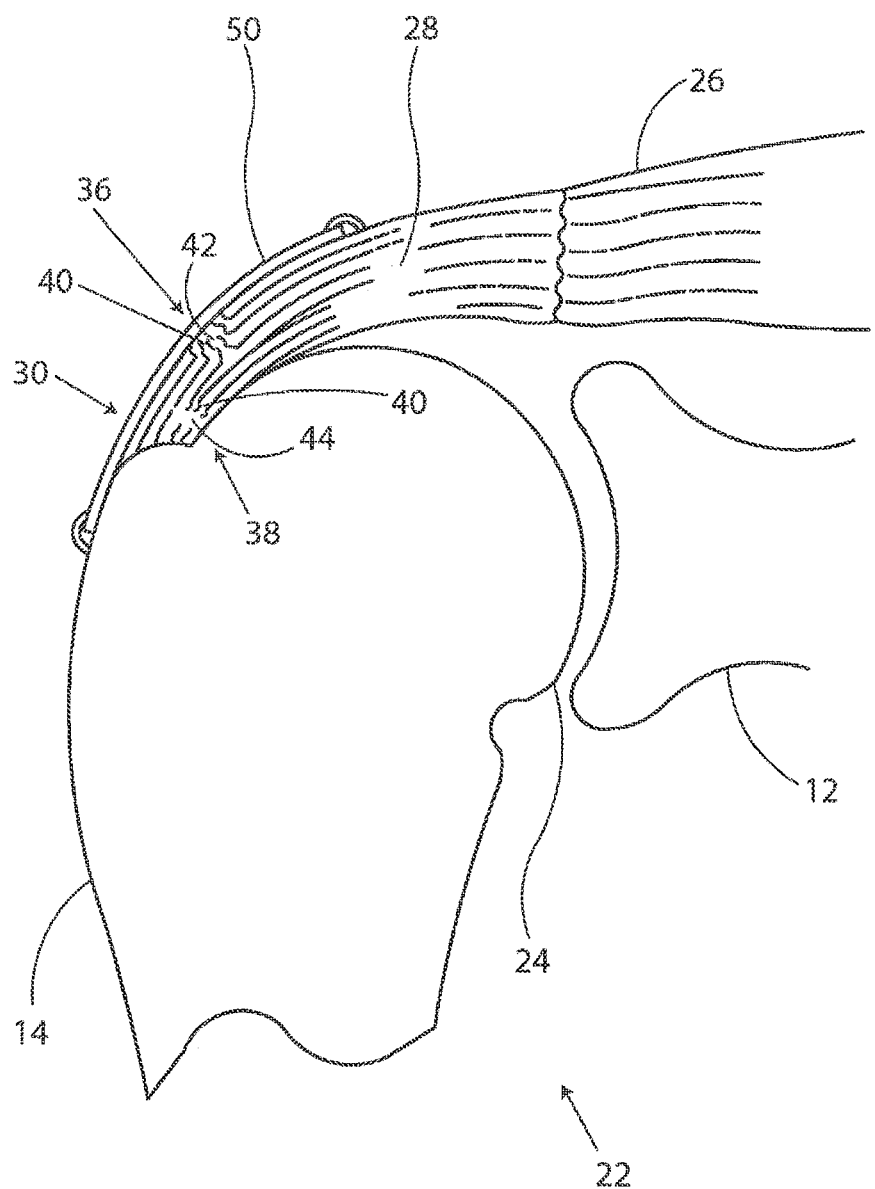
FIG. 4 is a stylized anterior view of a shoulder including a humerus and a scapula. The head of the humerus is shown mating with the glenoid fossa of the scapula at a glenohumeral joint.

FIG. 4 is a stylized anterior view of a shoulder 22 including a humerus 14 and a scapula 12. In FIG. 4, a head 24 of humerus 14 is shown mating with a glenoid fossa of scapula 12 at a glenohumeral joint. A supraspinatus 26 is also shown in FIG. 4. This muscle, along with others, control the movement of humerus 14 relative to scapula 12. A distal tendon 28 of supraspinatus 26 meets humerus 14 at an insertion point 30.

In the embodiment of FIG. 4, distal tendon 28 includes a first damaged portion 36. A number of loose tendon fibers 40 in first damaged portion 36 are visible in FIG. 4. First damaged portion 36 includes a first tear 42 extending partially through distal tendon 28. First tear 42 may therefore be referred to as a partial thickness tear. With reference to FIG. 4, it will be appreciated that first tear 42 begins on the side of distal tendon 28 facing the subacromial bursa (shown in the previous Figure) and ends midway through distal tendon 28. Accordingly, first tear 42 may be referred to as a bursal side tear.

With reference to FIG. 4, it will be appreciated that distal tendon 28 includes a second damaged portion 38 located near insertion point 30. In the embodiment of FIG. 4, second damaged portion 38 of distal tendon 28 has become frayed and a number of loose tendon fibers 40 are visible in FIG. 4. Second damaged portion 38 of distal tendon 28 includes second tear 44. With reference to FIG. 4, it will be appreciated that second tear 44 begins on the side of distal tendon 28 facing the humerus 14. Accordingly, second damaged portion 38 may be referred to as an articular side tear.

In the embodiment of FIG. 4, a sheet-like implant 50 has been placed over the bursal side of distal tendon 28. With reference to FIG. 4, it will be appreciated that sheet-like implant 50 extends over insertion point 30, first tear 42 and second tear 44. Some useful methods in accordance with this detailed description may include placing a tendon repair implant on the bursal side of a tendon regardless of whether the tears being treated are on the bursal side, articular side or within the tendon. In some cases the exact location and nature of the tears being treated may be unknown. A tendon repair implant may be applied to the bursal side of a tendon to treat shoulder pain that is most likely caused by one or more partial thickness tears in the tendon. In the embodiment of FIG. 4, sheet-like implant 50 is fixed to distal tendon 28 by a plurality of staples.

Figure 5:
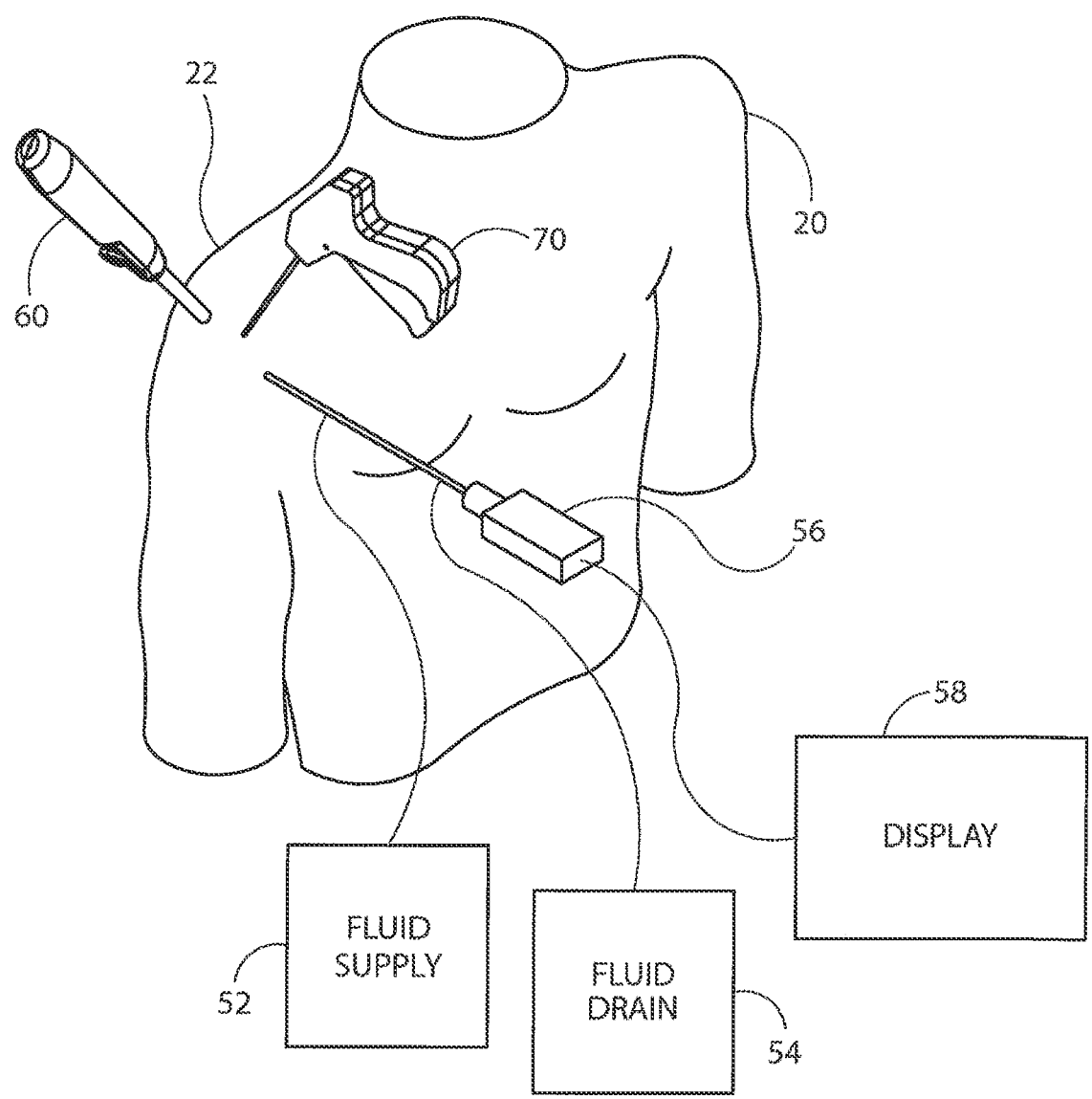
FIG. 5 is a stylized perspective view illustrating an exemplary procedure for treating a shoulder of a patient.

FIG. 5 is a stylized perspective view illustrating an exemplary procedure for treating a shoulder 22 of a patient 20. The procedure illustrated in FIG. 5 may include, for example, fixing tendon repair implants to one or more tendons of shoulder 22. The tendons treated may be torn, partially torn, have internal micro-tears, be untorn, and/or be thinned due to age, injury or overuse.

Shoulder 22 of FIG. 5 has been inflated to create a cavity therein. In the exemplary embodiment of FIG. 5, a fluid supply 52 is pumping a continuous flow of saline into the cavity. This flow of saline exits the cavity via a fluid drain 54. A camera 56 provides images from inside the cavity. The images provided by camera 56 may be viewed on a display 58.

Camera 56 may be used to visually inspect the tendons of shoulder 22 for damage. A tendon repair implant in accordance with this disclosure may be fixed to a bursal surface of the tendon regardless of whether there are visible signs of tendon damage. Applicants believe that the methods and apparatus of the present application and related devices may provide very beneficial therapeutic effect on a patient experiencing joint pain believed to be caused by internal microtears, but having no clear signs of tendon tears. By applying a tendon repair implant early before a full tear or other injury develops, the implant may cause the tendon to thicken and/or at least partially repair itself, thereby avoiding more extensive joint damage, pain, and the need for more extensive joint repair surgery.

A delivery system 60 can be seen extending from shoulder 22 in FIG. 5. Delivery system 60 comprises a sheath that is fixed to a handle. The sheath defines a lumen and a distal opening fluidly communicating with the lumen. In the embodiment of FIG. 5, the distal opening of the sheath has been placed in fluid communication with the cavity created in shoulder 22.

A tendon repair implant is at least partially disposed in the lumen defined by the sheath of delivery system 60. Delivery system 60 can be used to place the tendon repair implant inside shoulder 22. Delivery system 60 can also be used to hold the tendon repair implant against the tendon. In some embodiments, the tendon repair implant is folded into a compact configuration when inside the lumen of the sheath. When this is the case, delivery system 60 may be used to unfold the tendon repair implant into an expanded shape.

The tendon repair implant may be fixed to the tendon while it is held against the tendon by delivery system 60. Various attachment elements may be used to fix the tendon repair implant to the tendon. Examples of attachment elements that may be suitable in some applications include sutures, tissue anchors, bone anchors, and staples. In the exemplary embodiment of FIG. 5, the shaft of a fixation tool 70 is shown extending into shoulder 22. In one exemplary embodiment, fixation tool 70 is capable of fixing the tendon repair implant to the tendon with one or more staples while the tendon repair implant is held against the tendon by delivery system 60.

Figure 6:
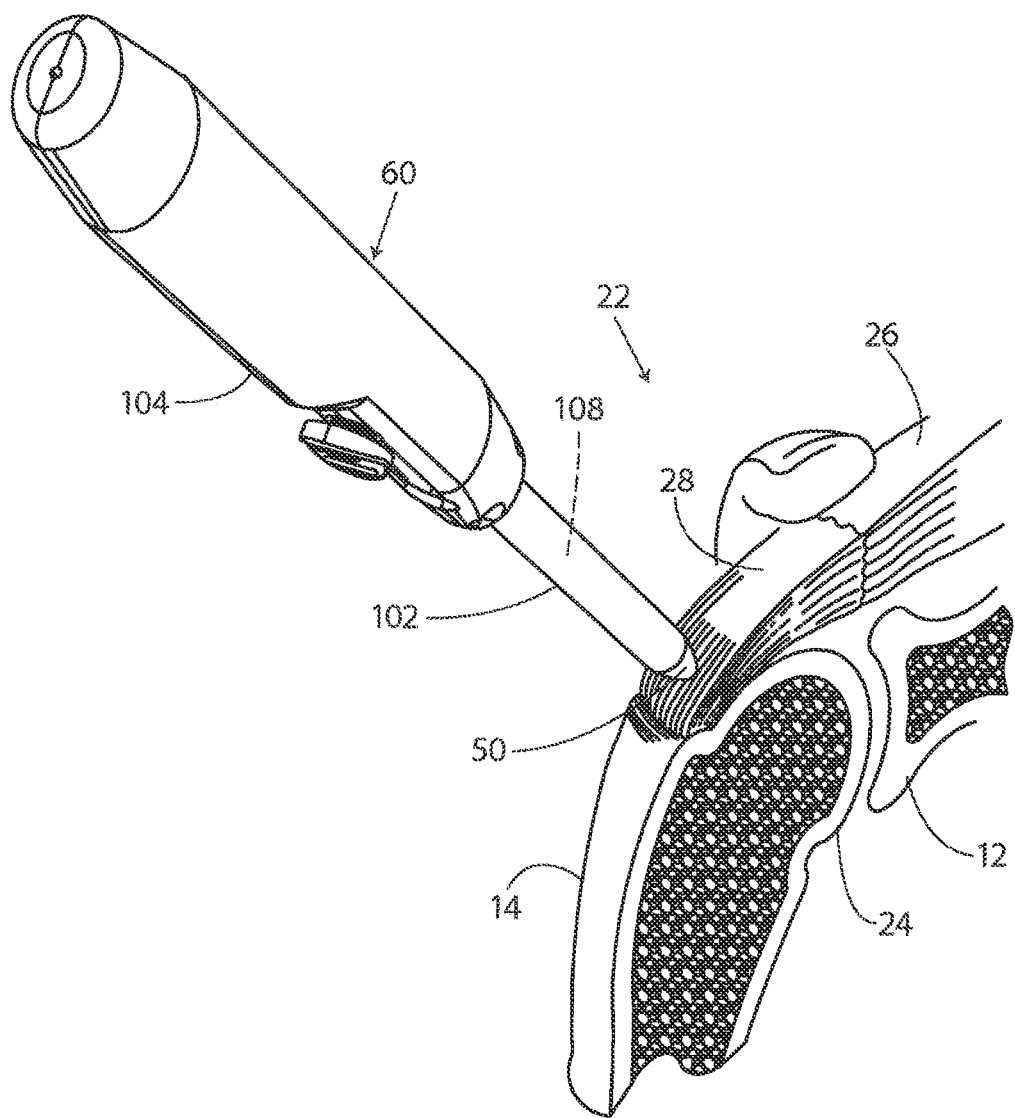
FIG. 6 is an enlarged perspective view further illustrating the procedure shown in the previous Figure.

FIG. 6 is an enlarged perspective view further illustrating the procedure shown in the previous Figure. FIG. 6 also illustrates the interior structure of shoulder 22 shown in the previous Figure. With reference to FIG. 6, it will be appreciated that shoulder 22 includes a humerus 14 and a scapula 12. In FIG. 6, a head 24 of humerus 14 is shown mating with a glenoid fossa of scapula 12 at a glenohumeral joint. A supraspinatus 26 is also shown in FIG. 6. A distal tendon 28 of supraspinatus 26 can be seen meeting a tuberosity of humerus 14 in FIG. 6.

Delivery system 60 is also shown in FIG. 6. In the embodiment of FIG. 6, a distal end of delivery system 60 has been positioned near distal tendon 28 of supraspinatus 26. Delivery system 60 comprises a sheath 102 that is fixed to a handle 104. Sheath 102 defines a lumen 108 and a distal opening fluidly communicating with the lumen. In the embodiment of FIG. 6, a central portion of a sheet-like implant 50 can be seen extending through the distal opening defined by sheath 102. In the embodiment of FIG. 6, sheet-like implant 50 is overlaying an implant expander. The implant expander and sheet-like implant 50 are both assuming a compact configuration. The majority of sheet-like implant 50 is disposed inside sheath 102. A central portion of sheet-like implant 50 is extending out of sheath 102. This central portion of sheet-like implant 50 is contacting an outer surface of distal tendon 28 in the embodiment of FIG. 6.

Figure 7:
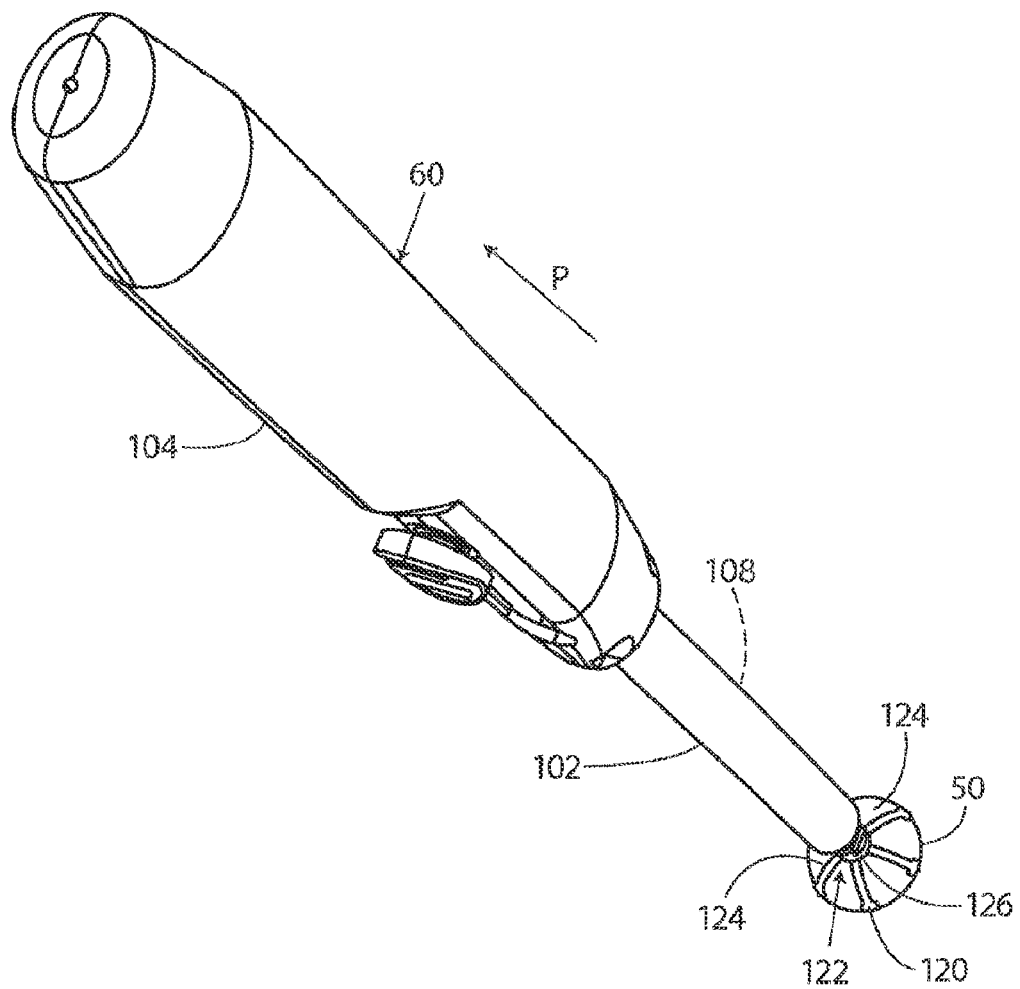
FIG. 7 is an enlarged perspective view showing the delivery system shown in the previous Figure.

FIG. 7 is an enlarged perspective view showing delivery system 60 shown in the previous Figure. In the embodiment of FIG. 7, sheath 102 of delivery system 60 has been moved in a proximal direction P relative to handle 104. By comparing FIG. 7 to the previous Figure, it will be appreciated that sheet-like implant 50 and implant expander 120 are now disposed outside of lumen 108 defined by sheath 102. Implant expander 120 comprises a central portion 122 and a plurality of leg portions 124 radiating from central portion 122. In FIG. 7, leg portions 124 of implant expander 120 are shown overlaying sheet-like implant 50. Hub 126 is shown overlaying central portion 122 of implant expander 120 in FIG. 7. Implant expander 120 can be used to expand sheet-like implant 50 and hold sheet-like implant 50 against the surface of a target tissue. Sheet-like implant 50 may be fixed to the target tissue while the implant is held against the target tissue by implant expander 120.

Figure 8:
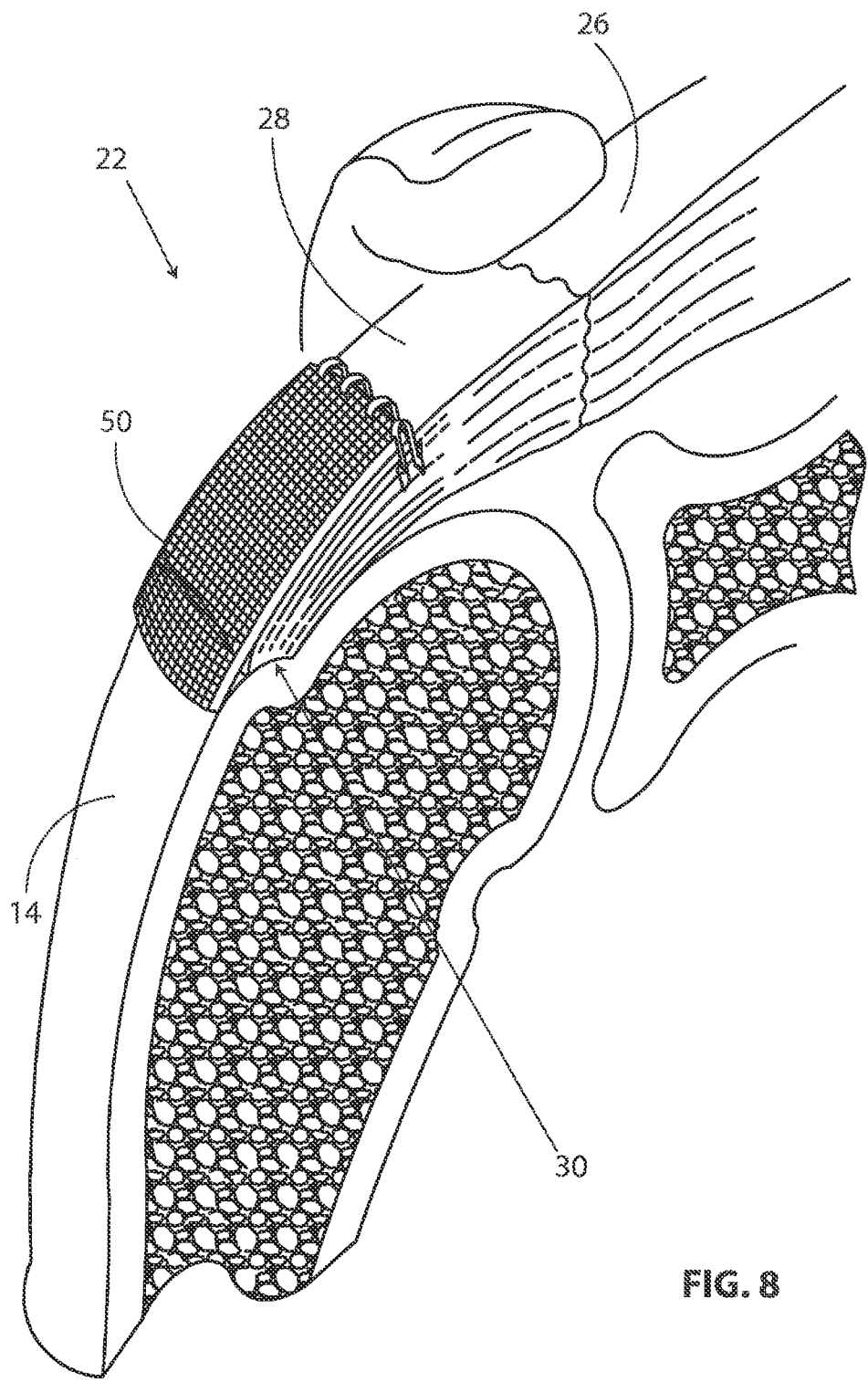
FIG. 8 is a stylized perspective view of a shoulder including a supraspinatus muscle having a distal tendon.

FIG. 8 is a stylized perspective view of a shoulder 22 including a supraspinatus 26 having a distal tendon 28. With reference to FIG. 8, it will be appreciated that a tendon repair implant 50 has been fixed to a surface of distal tendon 28. Tendon repair implant 50 may comprise, for example, various sheet-like structures without deviating from the spirit and scope of the present detailed description. In some useful embodiments, the sheet-like structure may comprise a plurality of fibers. The fibers may be interlinked with one another. When this is the case, the sheet-like structure may comprise a plurality of apertures comprising the interstitial spaces between fibers. Various processes may be used to interlink the fibers with one another. Examples of processes that may be suitable in some applications including weaving, knitting, and braiding. In some embodiment, the sheet-like structure may comprise a laminate including multiple layers of film with each layer of film defining a plurality of micro-machined or formed holes. The sheet-like structure of the tendon repair implant may also comprise a plurality of electro-spun nanofiber filaments forming a composite sheet. Additionally, the sheet-like structure may comprise a synthetic sponge material that defines a plurality of pores. The sheet-like structure may also comprise a reticulated foam material. Reticulated foam materials that may be suitable in some applications are available from Biomerix Corporation of Fremont, Calif. which identifies these materials using the trademark BIOMATERIAL™. The sheet-like structure may be circular, oval, oblong, square, rectangular, or other shape configured to suit the target anatomy.

Various attachment elements may be used to fix tendon repair implant 50 to distal tendon 28 without deviating from the spirit and scope of this detailed description. Examples of attachment elements that may be suitable in some applications include sutures, tissue anchors, bone anchors, and staples. In the exemplary embodiment of FIG. 8, a plurality of staples are fixing tendon repair implant 50 to distal tendon 28. In some exemplary methods, a plurality of staples may be applied using a fixation tool. The fixation tool may then be withdrawn from the body of the patient. Distal tendon 28 meets humerus 14 at an insertion point 30. With reference to FIG. 8, it will be appreciated that sheet-like implant 50 extends over insertion point 30. Tendon repair implant may be applied to distal tendon 28, for example, using the procedure illustrated in the previous Figure. In various embodiments, staples may straddle the perimeter edge of the sheet-like implant (as shown in FIG. 8), may be applied adjacent to the perimeter, and/or be applied to a central region of the implant. In some embodiments, the staples may be used to attach the implant to soft tissue and/or to bone.

Figure 9:
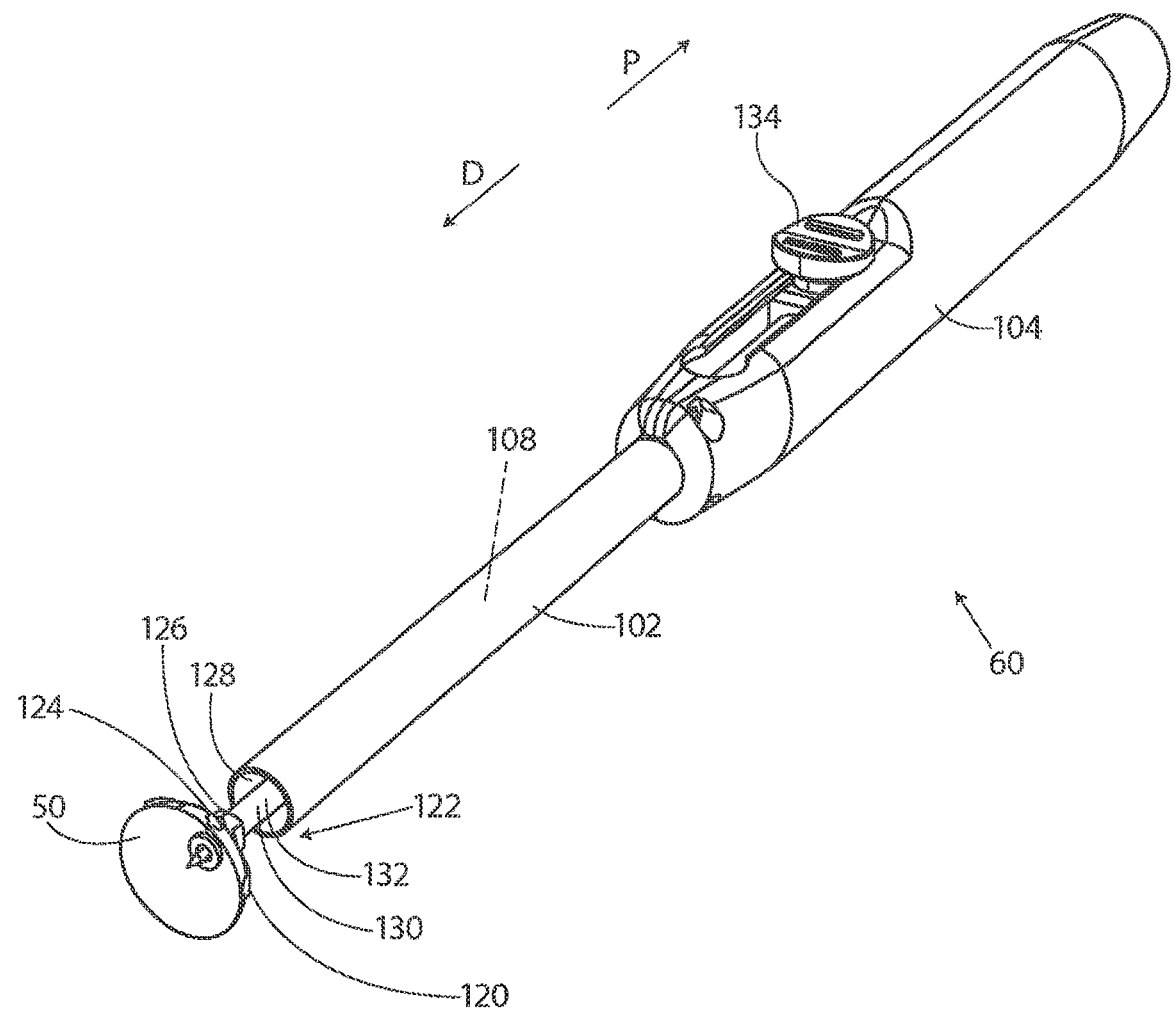
FIG. 9 is an additional perspective view further illustrating a delivery system in accordance with this disclosure.

FIG. 9 is an additional perspective view further illustrating delivery system 60. Delivery system 60 comprises a sheath 102 that is fixed to a handle 104. Sheath 102 defines a lumen 108 and a distal opening 128 fluidly communicating with lumen 108. In the embodiment of FIG. 9, a delivery aid 130 can be seen extending through distal opening 128 defined by sheath 102.

In the embodiment of FIG. 9, delivery aid 130 comprises a hub 126 that is disposed at the distal end of a control rod 132. An implant expander 120 is attached to hub 126. Implant expander 120 comprises a central portion 122 and a plurality of leg portions 124 radiating from central portion 122. In FIG. 9, a sheet-like implant 50 is shown overlaying a distal surface of implant expander 120. In the exemplary embodiment of FIG. 9, implant expander 120 is urging sheet-like implant 50 against a generally spherical surface (not shown in FIG. 9).

Sheath 102 of delivery system 60 is coupled to a button 134. It will be appreciated that various other operative mechanisms may be used in addition to button 134. Relative motion between button 134 and handle 104 will cause similar relative motion between sheath 102 and handle 104. In the exemplary embodiment of FIG. 9, sheath 102 will be moved distally (relative to handle 104) when button 134 is moved distally (relative to handle 104). Additionally, sheath 102 will be moved proximally (relative to handle 104) when button 134 is moved proximally (relative to handle 104).

In FIG. 9, implant expander 120 is shown residing outside of lumen 108 defined by sheath 102. In FIG. 9, implant expander 120 is shown assuming a deployed configuration. Implant expander 120 can be selectively urged to assume a compact configuration, for example, by placing implant expander inside lumen 108 defined by sheath 102. Implant expander can be placed inside lumen 108, for example, by advancing sheath 102 over implant expander 120.

FIG. 10A through FIG. 10E are a series of stylized plan views illustrating an exemplary method in accordance with the present detailed description. FIG. 10A through FIG. 10E may be referred to collectively as FIG. 10. A proximal direction is illustrated with an arrow P in FIG. 10. A distal direction is illustrated with another arrow D in FIG. 10. The exemplary method of FIG. 10 may be used, for example, to fix a sheet-like implant 50 to a surface 136 of a target tissue 138.

Figure 10A:
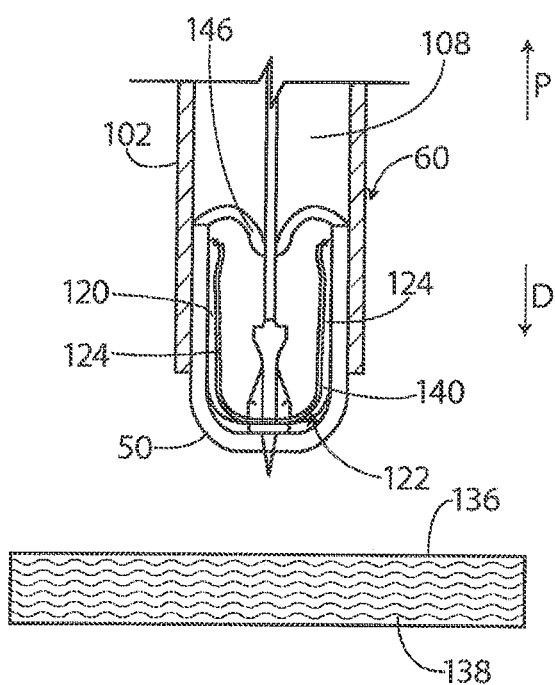
FIG. 10A through FIG. 10E are a series of stylized plan views illustrating an exemplary method in accordance with the present detailed description.

FIG. 10A is a partial cross-sectional view illustrating a distal portion of a delivery system 60 in accordance with this detailed description. In the embodiment of FIG. 10, the distal portion of delivery system 60 has been positioned near a target tissue 138. Delivery system 60 comprises a sheath 102 that is fixed to a handle. Sheath 102 defines a lumen 108 and a distal opening fluidly communicating with the lumen. In the embodiment of FIG. 10A, a central portion of a sheet-like implant 50 can be seen extending through the distal opening defined by sheath 102. In the embodiment of FIG. 10, sheet-like implant 50 is overlaying an implant expander. The implant expander and sheet-like implant 50 are both assuming a compact configuration. With reference to FIG. 10, it will be appreciated that the majority of sheet-like implant 50 is disposed inside sheath 102. A central portion of a sheet-like implant 50 is extending out of sheath 102.

Implant expander 120 of FIG. 10 comprises a central portion 122 and a plurality of leg portions 124 radiating from central portion 122. In the embodiment of FIG. 10A, implant expander 120 is assuming a first compact configuration. With reference to FIG. 10A, it will be appreciated that the free end of each leg portion 124 is disposed proximally of central portion 122 when implant expander 120 is assuming the first compact configuration. With continuing reference to FIG. 10, it will be appreciated that a distal surface 140 of implant expander 120 defines a convex surface when implant expander 120 is assuming the first compact configuration 142. Portions of sheet-like implant 50 can be seen extending between leg portions 124 of implant expander 120 and the wall of sheath 102. In FIG. 10, a fold 146 comprising a portion of sheet-like implant 50 can also be seen extending between an adjacent pair of leg portions 124.

Figure 10B:
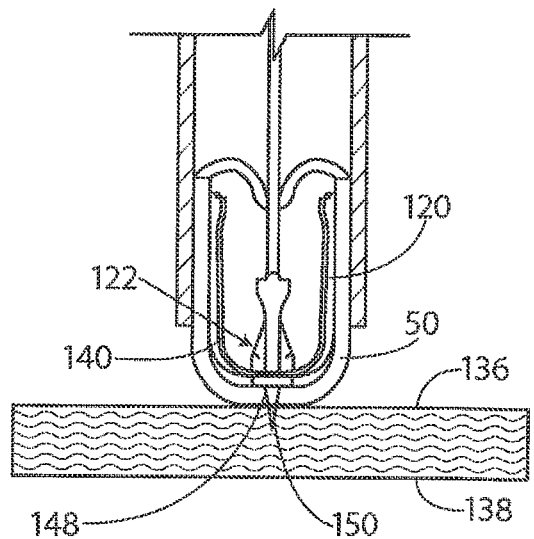

In the embodiment of FIG. 10B, a central portion of sheet-like implant 50 is trapped between implant expander 120 and surface 136 of target tissue 138. By comparing FIG. 10A and FIG. 10B, it will be appreciated that sheet-like implant 50 has been advanced distally so that central portion of sheet-like implant 50 is contacting surface 136 of target tissue 138.

In the embodiment of FIG. 10B, delivery system 60 includes a projection 148 extending distally from distal surface 140 of central portion 122 of implant expander 120. In some applications, projection 148 may be used to temporarily hold the position of delivery system 60 while sheet-like implant 50 is held against surface 136 of target tissue 138. In the exemplary embodiment of FIG. 10B, projection 148 comprises a spike 150 having a generally cone-like shape. In the embodiment of FIG. 10B, spike 150 has been advanced so that a distal portion of spike 150 has pierced target tissue 138. Spike 150 can be seen extending through sheet-like implant 50 in FIG. 10B. Spike 150 may be used to temporarily center implant expander 120 and sheet-like implant 50 on a target location. Once sheet-like implant 50 has been fixed to target tissue 138, spike 150 can be withdrawn from target tissue 138 and sheet-like implant 50.

Figure 10C:
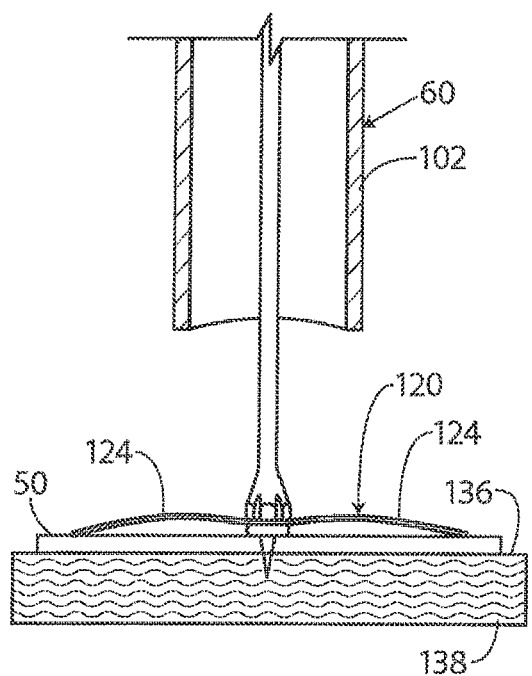

In FIG. 10C, implant expander 120 of delivery system 60 is shown assuming a deployed configuration. By comparing FIG. 10C and FIG. 10B, it will be appreciated that sheath 102 has been retracted in proximal direction P. In the embodiment of FIG. 10C, leg portions 124 of implant expander 120 are conforming to the shape of surface 136. In the exemplary embodiment of FIG. 10, surface 136 has a generally planar shape. Sheet-like implant 50 is resting between implant expander 120 and surface 136 of target tissue 138, with sheet-like implant 50 overlaying surface 136. With reference to FIG. 10C, it will be appreciated that implant expander 120 is causing sheet-like implant 50 to generally conform to the shape of surface 136.

Figure 10D:
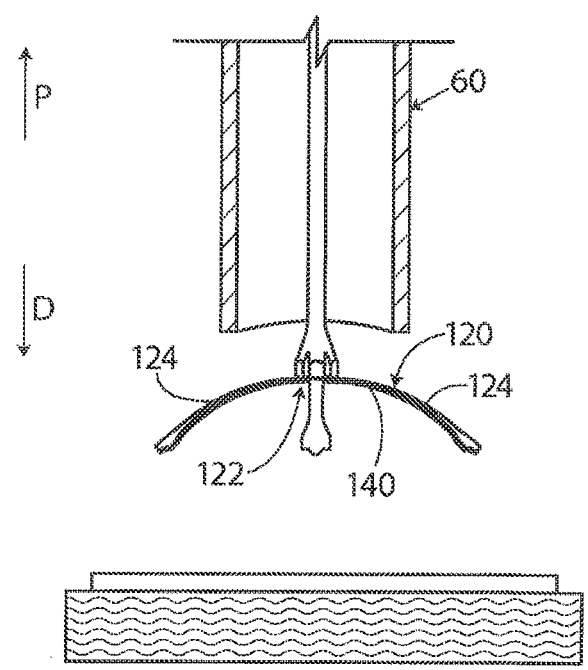

In FIG. 10D, implant expander 120 of delivery system 60 is shown assuming an unstressed configuration. By comparing FIG. 10C and FIG. 10D, it will be appreciated that implant expander 120 has been lifted in proximal direction P. In the embodiment of FIG. 10D, no external forces are acting on leg portions 124 and implant expander 120 is free to assume the unstressed configuration shown in FIG. 10D. With reference to FIG. 10D, it will be appreciated that the free end of each leg portion 124 is disposed distally of central portion 122 when implant expander 120 is assuming the unstressed configuration. With continuing reference to FIG. 10, it will be appreciated that the distal surface 140 of implant expander 120 defines a concave surface when implant expander 120 is assuming the unstressed configuration.

Figure 10E:
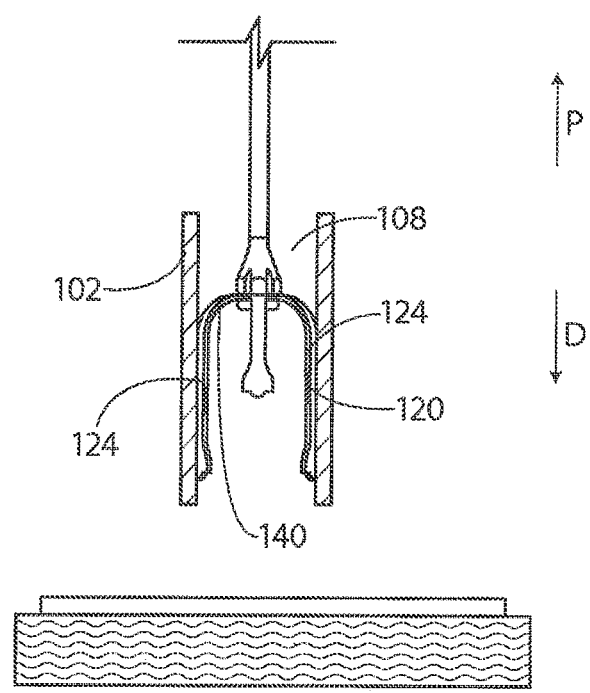

In FIG. 10E, implant expander 120 of delivery system 60 is shown assuming a second compact configuration. By comparing FIG. 10E and FIG. 10D, it will be appreciated that implant expander 120 and sheath 102 have been moved relative to each other. With reference to FIG. 10E, it will be appreciated that implant expander 120 may be urged to assume the second compact configuration moving implant expander 120 and sheath 102 relative to one another so that implant expander 120 is disposed in lumen 108 defined by sheath 102. With reference to FIG. 10, it will be appreciated that the free end of each leg portion 124 is disposed distally of central portion 122 when implant expander 120 is assuming the second compact configuration 144. With continuing reference to FIG. 10, it will be appreciated that the distal surface 140 of implant expander 120 defines a concave surface when implant expander 120 is assuming the second compact configuration 144.

Figure 11:
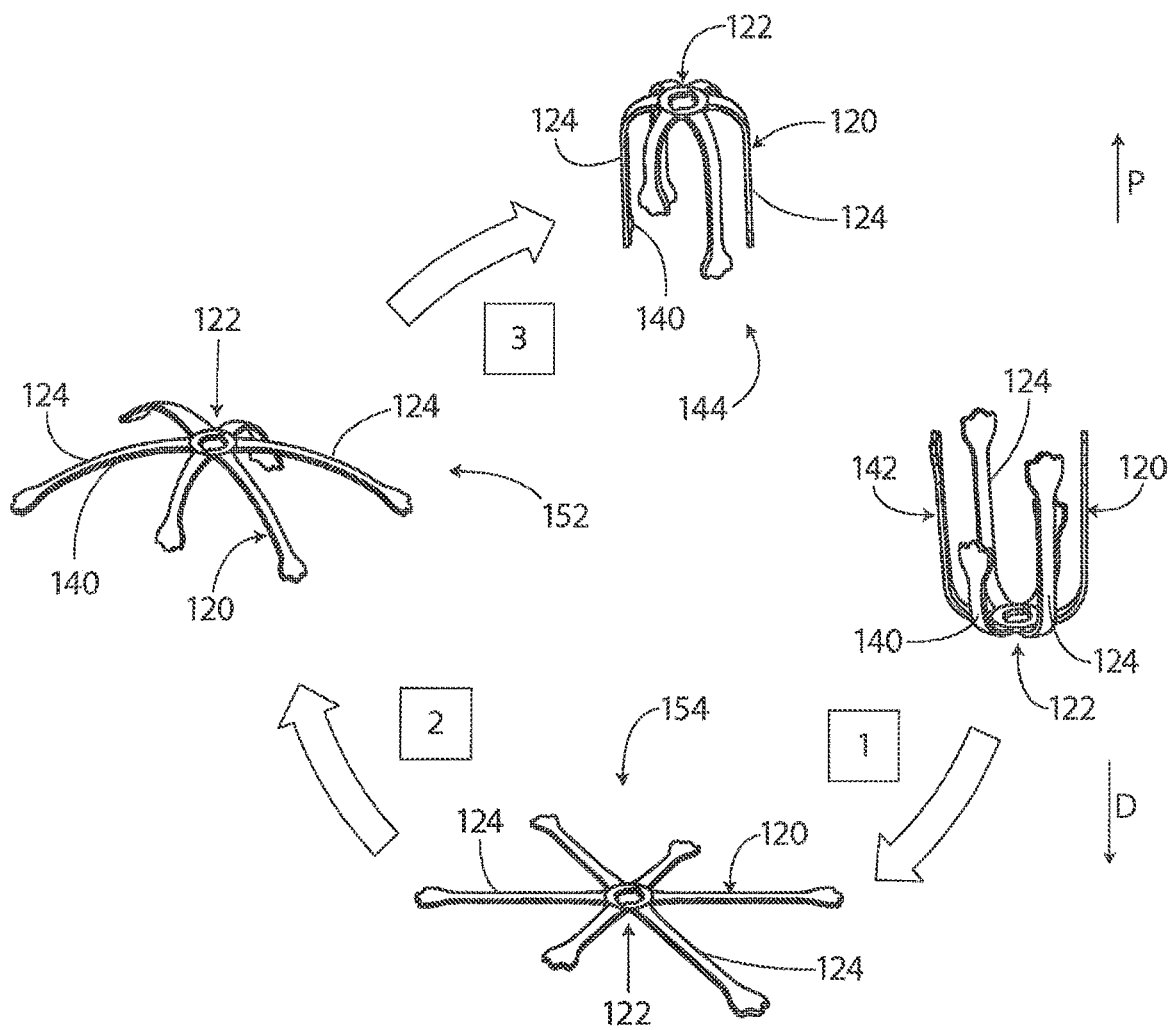
FIG. 11 is a stylized diagram illustrating four configurations of an exemplary implant expander.

FIG. 11 is a stylized diagram illustrating four configurations of an exemplary implant expander 120. The step of transitioning between one configuration and another configuration is represented by three arrows in FIG. 11. A proximal direction is illustrated with another arrow P in FIG. 11. A distal direction is illustrated with an additional arrow D in FIG. 11.

Implant expander 120 of FIG. 11 comprises a central portion 122 and a plurality of leg portions 124 radiating from central portion 122. A first arrow 1 represents a transition between a first compact configuration 142 and a deployed configuration 154. With reference to FIG. 11, it will be appreciated that the free end of each leg portion 124 is disposed proximally of central portion 122 when implant expander 120 is assuming the first compact configuration 142. With continuing reference to FIG. 11, it will be appreciated that a distal surface 140 of implant expander 120 defines a convex surface when implant expander 120 is assuming the first compact configuration 142. In some exemplary methods, implant expander 120 is held in the first compact configuration 142 while implant expander 120 is disposed in a lumen of a sheath. In these exemplary methods, implant expander 120 may be allowed to assume deployed configuration 154 when the sheath is retracted from around implant expander 120. Implant expander 120 may also be allowed to assume deployed configuration 154 when implant expander 120 is moved in a distal direction so that implant expander 120 exits the lumen via a distal opening of the sheath or when the sheath moves proximally to reveal the implant expander from within the distal opening of the sheath and relieve stress within leg portions 124.

In the exemplary embodiment of FIG. 11, leg portions 124 of implant expander 120 conform to the shape of a target tissue when implant expander 120 is in the deployed configuration. In FIG. 11, implant expander 120 is shown conforming to the shape of a generally planar surface (not shown in FIG. 11) while implant expander is assuming the deployed configuration. A second arrow 2 represents a transition between the deployed configuration 154 and an unstressed configuration 152. In some exemplary methods, implant expander 120 is free to assume unstressed configuration 152 when implant expander 120 is lifted off of a target surface so that no external forces are acting on leg portions 124 of implant expander 120. With reference to FIG. 11, it will be appreciated that the free end of each leg portion 124 is disposed distally of central portion 122 when implant expander 120 is assuming unstressed configuration 152. With continuing reference to FIG. 11, it will be appreciated that the distal surface 140 of implant expander 120 defines a concave surface when implant expander 120 is assuming the unstressed configuration 152.

A third arrow 3 represents a transition between the unstressed configuration 152 and a second compact configuration 144. In some exemplary methods, implant expander 120 is urged to assume second compact configuration 144 by drawing implant expander 120 proximally into a lumen of a sheath. With reference to FIG. 11, it will be appreciated that the free end of each leg portion 124 is disposed distally of central portion 122 when implant expander 120 is assuming the second compact configuration 144. With continuing reference to FIG. 11, it will be appreciated that the distal surface 140 of implant expander 120 defines a concave surface when implant expander 120 is assuming the second compact configuration 144.

Figure 12:
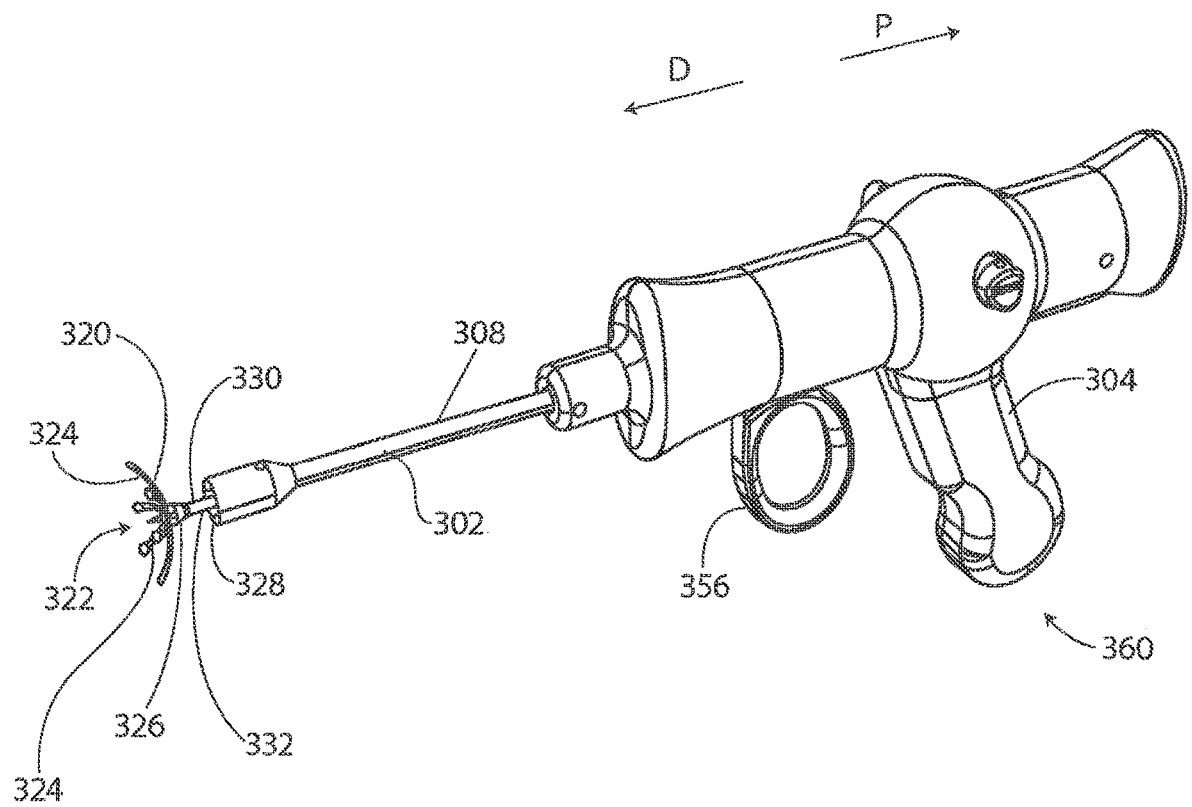
FIG. 12 is a perspective view illustrating an exemplary delivery system in accordance with this disclosure.

FIG. 12 is a perspective view illustrating an exemplary delivery system 360. Delivery system 360 comprises a sheath 302 that is fixed to a handle 304. Sheath 302 defines a lumen 308 and a distal opening 328 fluidly communicating with lumen 308. In the embodiment of FIG. 12, a delivery aid 330 can be seen extending through distal opening 328 defined by sheath 302. In the embodiment of FIG. 12, delivery aid 330 comprises a hub 326 that is disposed at the distal end of a control rod 332. An implant expander 320 is attached to hub 326. Implant expander 320 comprises a central portion 322 and a plurality of leg portions 324 radiating from central portion 322.

Sheath 302 of delivery system 360 is coupled to an actuator 356. Relative motion between actuator 356 and handle 304 will cause similar relative motion between sheath 302 and handle 304. In the exemplary embodiment of FIG. 12, sheath 302 will be moved distally (relative to handle 304) when actuator 356 is moved distally (relative to handle 304). Additionally, sheath 302 will be moved proximally (relative to handle 304) when actuator 356 is moved proximally (relative to handle 304).

In FIG. 12, implant expander 320 is shown residing outside of lumen 308 defined by sheath 302. In FIG. 12, implant expander 320 is shown assuming an unstressed configuration. Implant expander 320 can be selectively urged to assume a compact configuration, for example, by placing implant expander inside lumen 308 defined by sheath 302. Implant expander can be placed inside lumen 308, for example, by advancing sheath 302 over implant expander 320.

Figure 13:
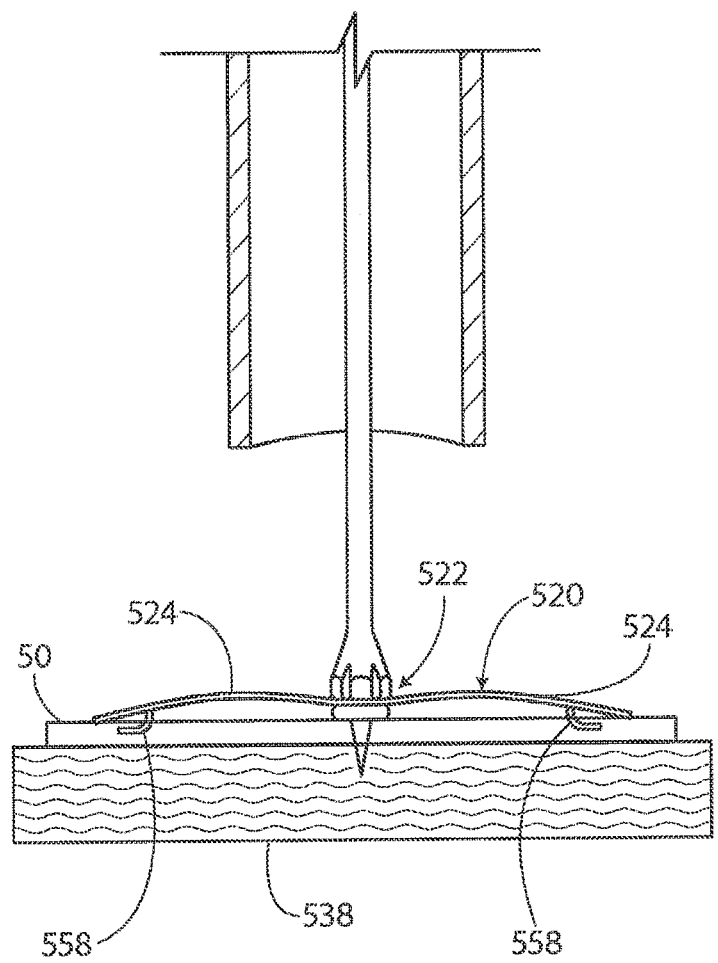
FIG. 13 is a plan view illustrating an exemplary assembly in accordance with the present detailed description.

FIG. 13 is a plan view illustrating an exemplary assembly in accordance with the present detailed description. The assembly of FIG. 13 includes a sheet-like implant 50 and an implant expander 520. Implant expander 520 of FIG. 13 comprises a central portion 522 and a plurality of leg portions 524 radiating from central portion 522. In the embodiment of FIG. 13, a sheet-like implant 50 is trapped between implant expander 520 and a target tissue 538. With reference to FIG. 13, it will be appreciated that implant expander 520 includes a plurality of retainers 558. In the embodiment of FIG. 13, retainers 558 engage sheet-like implant 50 so that sheet-like implant 50 moves when implant expander 520 is moved and may aid in imparting lateral stress of the legs into lateral stress within the implant.

Figure 14:
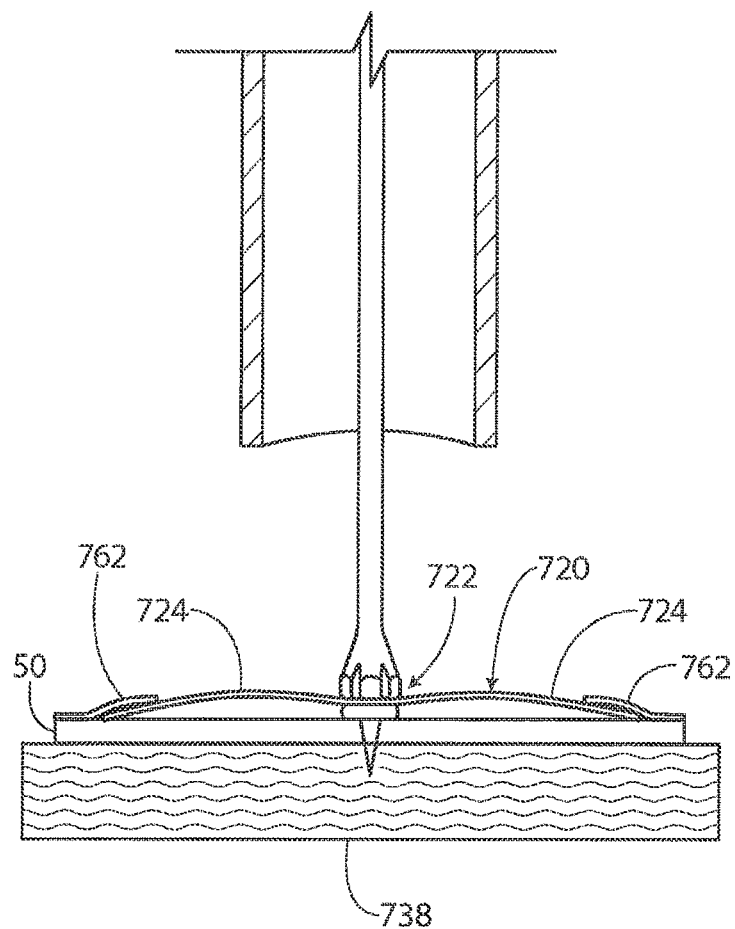
FIG. 14 is a plan view illustrating an exemplary assembly in accordance with the present detailed description.

IG. 14 is a plan view illustrating an exemplary assembly in accordance with the present detailed description. The assembly of FIG. 14 includes a sheet-like implant 50 and an implant expander 720. Implant expander 720 of FIG. 14 comprises a central portion 722 and a plurality of leg portions 724 radiating from central portion 722. In the embodiment of FIG. 14, a sheet-like implant 50 is trapped between implant expander 720 and a target tissue 738. With reference to FIG. 14, it will be appreciated that sheet-like implant 50 includes a plurality of pockets 762. In the embodiment of FIG. 14, each pocket 762 is dimensioned to receive the end of a leg portion 724 of implant expander 720. When this is the case, implant expander 720 engages pockets 762 so that sheet-like implant 50 moves when implant expander 720 is moved.

FIG. 15A through FIG. 15F are a series of stylized plan views illustrating an exemplary method in accordance with the present detailed description. FIG. 15A through FIG. 15F may be referred to collectively as FIG. 15. A proximal direction is illustrated with an arrow P in FIG. 15. A distal direction is illustrated with another arrow D in FIG. 15. The exemplary method of FIG. 15 may be used, for example, to fix a sheet-like implant 50 to a surface of a target tissue 138.

FIG. 15A is a stylized plan view of illustrating a shoulder 22 of a patient. Shoulder 22 of FIG. 15A has been inflated to create a cavity 62 therein. In the exemplary embodiment of FIG. 15A, a fluid supply 64 is pumping a continuous flow of saline into cavity 62. This flow of saline exits cavity 62 via a fluid drain 66.

In FIG. 15A, a sheath 102 of a delivery system 60 is shown positioned near a shoulder 22. Delivery system 60 also comprises a delivery aid 130 including an implant expander that is fixed to the distal end of a control rod 132. In the embodiment of FIG. 15A, a sheet-like implant 50 is overlaying the implant expander of delivery aid 130. In the embodiment of FIG. 15A, delivery aid 130 includes a projection 148 extending distally from the implant expander. In the exemplary embodiment of FIG. 15A, projection 148 comprises a spike 150 having a generally cone-like shape. Spike 150 can be seen extending through sheet-like implant 50 in FIG. 15A. Spike 150 may be used to temporarily center sheet-like implant 50 on a target location. Once sheet-like implant 50 has been fixed to target tissue 138, spike 150 can be withdrawn from target tissue 138 and sheet-like implant 50.

Delivery aid 130 can be used to insert sheet-like implant 50 into cavity 62 formed in shoulder 22. Delivery aid 130 can also be used to hold the sheet-like implant against a target tissue 138. In some embodiments, the sheet-like implant is folded into a compact configuration when inside the lumen of the sheath. When this is the case, delivery aid 130 may be used to unfold the sheet-like implant into an expanded shape.

In FIG. 15B, sheath 102 is shown extending into shoulder 22. A distal opening of sheath 102 has been placed in fluid communication with cavity 62 in the embodiment of FIG. 15B. By comparing FIG. 15A and FIG. 15B, it will be appreciated that sheet like implant 50 has been advanced distally so that a central portion of sheet like implant 50 is contacting a surface of target tissue 138. The central portion of sheet like implant 50 is trapped between implant expander 120 and the surface of target tissue 138 in the embodiment of FIG. 15B.

In FIG. 15C, implant expander 120 of delivery aid 130 is shown assuming a deployed configuration. By comparing FIG. 15C and FIG. 15B, it will be appreciated that sheath 102 has been retracted in a proximal direction P. Implant expander 120 of FIG. 15 comprises a central portion 122 and a plurality of leg portions 124 radiating from central portion 122. In the embodiment of FIG. 15B, implant expander 120 is assuming a deployed configuration. Implant expander 120 is fixed to the distal end of control rod 132 in the embodiment of FIG. 15.

Sheet like implant 50 is shown overlaying an outer surface of target tissue 138 in FIG. 15C. In the embodiment of FIG. 15C, sheet like implant 50 is generally conforming to the shape of target tissue 138. Implant expander 120 is holding sheet-like implant 50 against target tissue 138 in the embodiment of FIG. 15C.

Some exemplary methods in accordance with this detailed description include the steps of inflating a shoulder to create a cavity therein and placing a distal opening of a sheath in fluid communication with the cavity while the sheath is surrounding a delivery device disposed inside a lumen thereof and the sheath is maintaining the delivery device in a first compact configuration. A central portion of the sheet-like material may be placed in contact with a surface of a target tissue. The sheath may be withdrawn from around the delivery device so that the delivery device is free to assume a deployed configuration inside the cavity. The delivery device may be used to hold the sheet-like material against a surface of the target tissue while the delivery device is assuming the deployed configuration. The sheet-like implant 50 may be fixed to the target tissue while sheet-like implant 50 is held against the surface of the target tissue. The delivery device may be urged to assume a second compact configuration as the delivery device is removed from the cavity.

In FIG. 15D, a fixation tool shaft 72 of a fixation tool 70 is shown extending into shoulder 22. In FIG. 15D, a distal end of fixation tool shaft 72 is disposed proximate an edge of sheet like implant 50. One or more staples may be disposed inside fixation tool shaft 72. Fixation tool 70 may apply staples to fix sheet like implant 50 to target tissue 138 while sheet like implant 50 is held in place by implant expander 120.

Various attachment elements may be used to fix sheet like implant 50 to target tissue 138 without deviating from the spirit and scope of this detailed description. Examples of attachment elements that may be suitable in some applications include sutures, tissue anchors, bone anchors, and staples. In the exemplary embodiment of FIG. 15E, sheet like implant 50 is fixed to target tissue 138 by a plurality of staples 74. In some exemplary methods, a plurality of staples may be applied using a fixation tool. The fixation tool may then be withdrawn from the body of the patient. In the exemplary embodiment of FIG. 15E, delivery aid 130 may be used to hold sheet like implant 50 against target tissue 138 while staples 74 are applied using fixation tool 70.

With reference to FIG. 15F, it will be appreciated that delivery aid 130 has been withdrawn from shoulder 22 and retracted into lumen 108 defined by sheath 102. Implant expander 120 of delivery aid 130 has been urged to assume a second compact configuration in the embodiment of FIG. 15F. Implant expander 120 comprises a central portion 122 and a plurality of leg portions 124 radiating from central portion 122. With reference to FIG. 15F, it will be appreciated that the free end of each leg portion is disposed distally of central portion 122 when implant expander 120 is assuming the second compact configuration.

Figure 16:
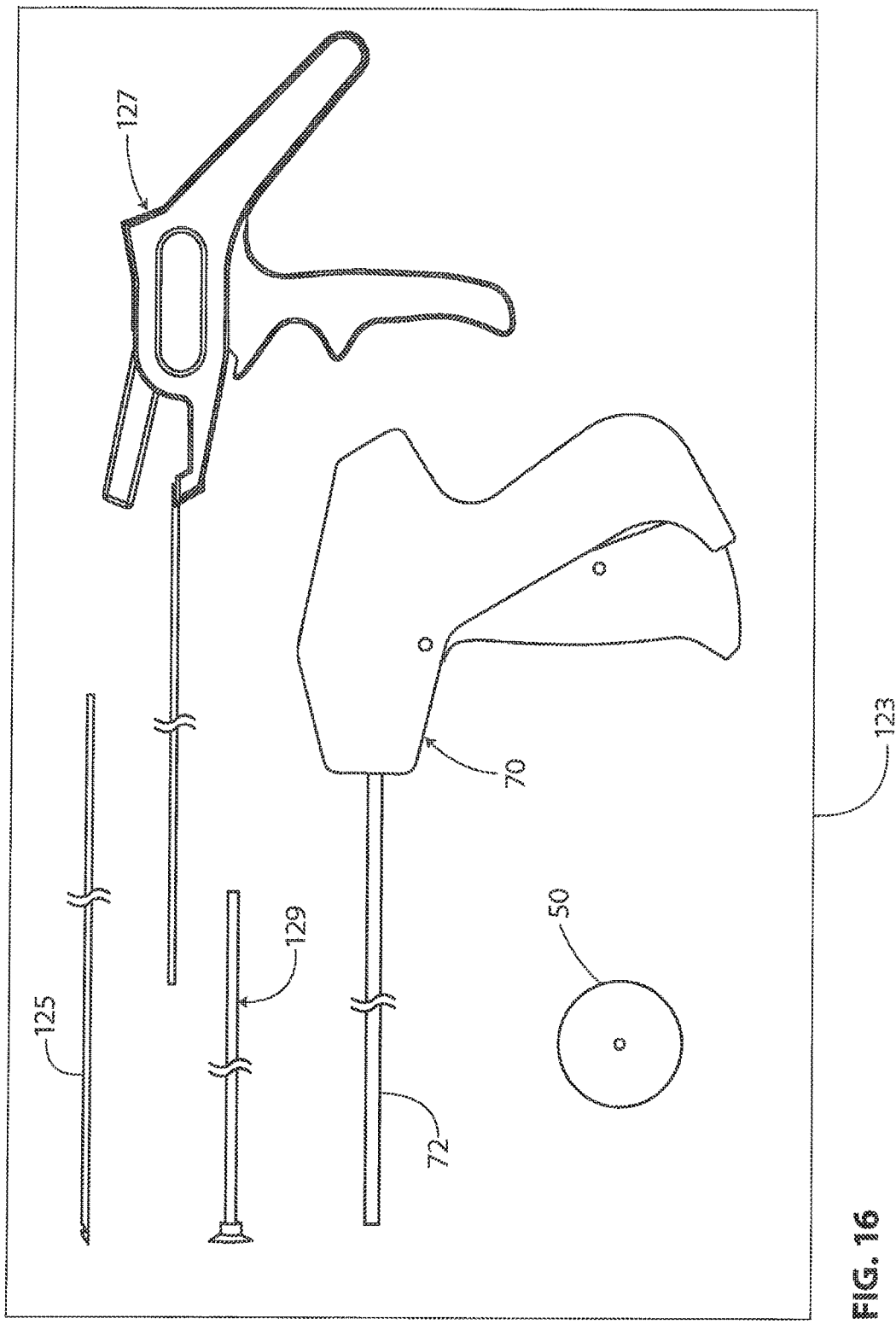
FIG. 16 is a stylized depiction of a kit that may be used, for example, for delivering a sheet-like implant to a target location within the body of a patient.

FIG. 16 is a stylized depiction of a kit 123. In the exemplary embodiment of FIG. 16, kit 123 comprises a sheet-like implant 50 and a number of tools that may be used in conjunction with sheet-like implant 50. The tools of kit 123 may be used, for example, for delivering sheet-like implant 50 to a target location within the body of a patient. These tools may also be used, for example, for fixing sheet-like implant 50 to a target tissue.

In the exemplary embodiment of FIG. 16, kit 123 comprises a locating guide 125, a locating guide removal tool 127, a fixation tool 70, and a delivery aid 129. In some useful embodiments, locating guide 125 includes a temporary fixation mechanism proximate its distal end. A method in accordance with the present detailed description may include temporarily fixing the distal end of locating guide 125 to a target tissue and advancing sheet-like implant 50 over locating guide 125 for delivering the sheet-like implant to the target location. In some applications, delivery aid 129 may be used for advancing sheet-like implant 50 over locating guide 125 and urging sheet-like implant 50 against a target tissue. Fixation tool 70 of kit 123 may be used, for example, for fixing sheet-like implant 50 to the target tissue. Locating guide removal tool 127 may be used to remove locating guide 125 after sheet-like implant 50 has been fixed to the target tissue. In the embodiment of FIG. 16, fixation tool 70 includes a fixation tool shaft 72.

Figure 17A:
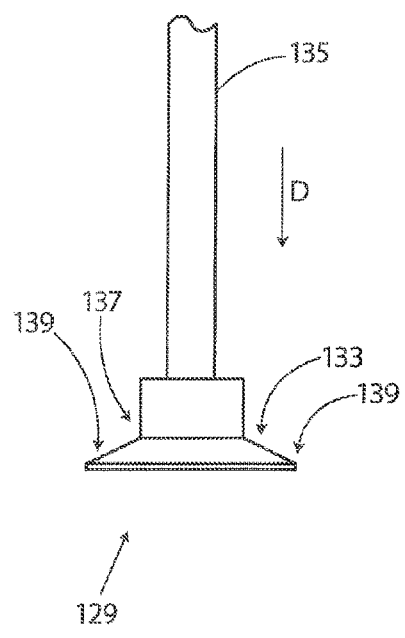
FIG. 17A is an enlarged plan view illustrating a delivery aid included in the kit of FIG. 16.
Figure 17B:
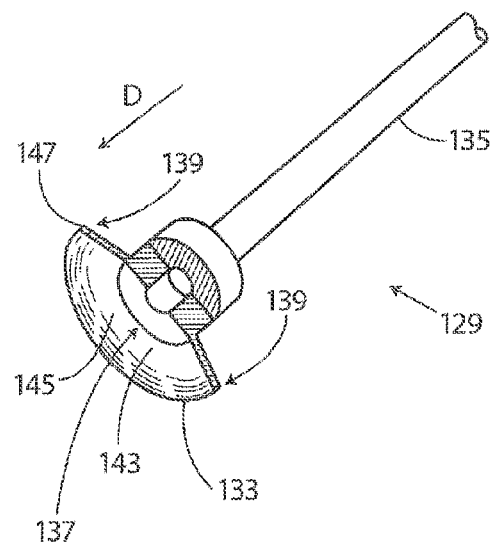
FIG. 17B is a partial cross-sectional perspective view further illustrating the delivery aid shown in FIG. 17A.

FIG. 17A is an enlarged plan view illustrating delivery aid 129 shown in the previous Figure. FIG. 17B is a partial cross-sectional perspective view further illustrating delivery aid 129. FIG. 17A and FIG. 17B may be collectively referred to as FIG. 17. A distal direction is illustrated with an arrow D in FIG. 17.

In the exemplary embodiment of FIG. 17, delivery aid 129 includes an implant expander 133 fixed to a distal end of a control rod 135. Implant expander 133 of FIG. 17 has a central portion 137 and an outer portion 139 extending radially from central portion 137. In the embodiment of FIG. 17, no external forces are acting on implant expander 133 and implant expander 133 is free to assume an unstressed configuration. With reference to FIG. 17B, it will be appreciated that a distal surface 143 of implant expander 133 comprises a generally concave surface 145 when the implant expander is assuming an unstressed configuration. With continuing reference to FIG. 17, it will be appreciated that an outermost edge 147 of outer portion 139 is disposed distally of central portion 137 when implant expander 133 is assuming the unstressed configuration.

FIG. 18A through FIG. 18I are a series of stylized plan views illustrating an exemplary method in accordance with the present detailed description. FIG. 18A through FIG. 18I may be referred to collectively as FIG. 18. A proximal direction is illustrated with an arrow P in FIG. 18. A distal direction is illustrated with another arrow D in FIG. 18. The exemplary method of FIG. 18 may be used, for example, to fix a sheet-like implant 50 to a surface of a target tissue 138.

Figure 18C:
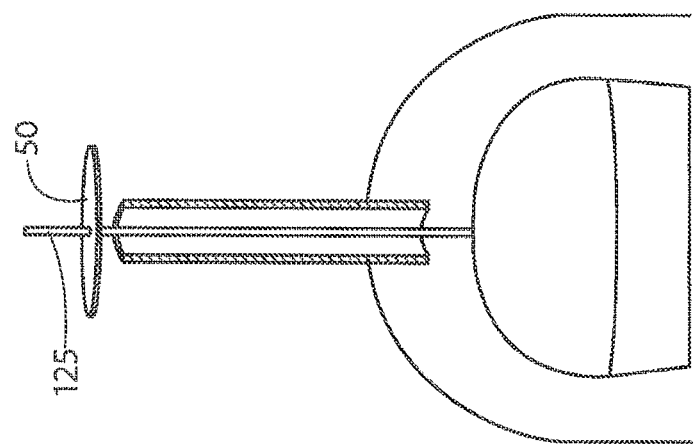
Figure 18B:
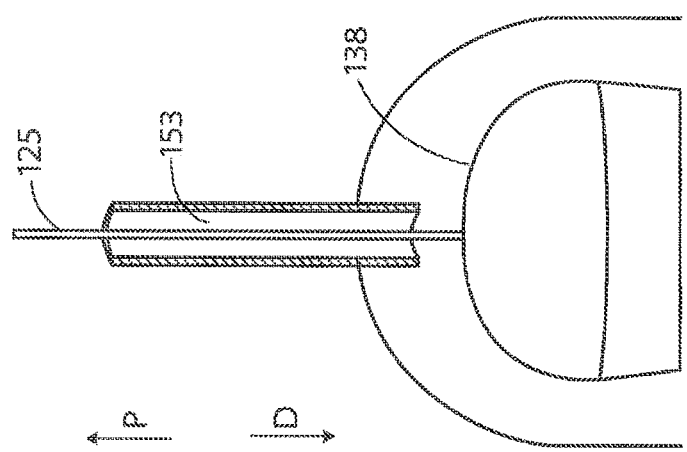
Figure 18A:
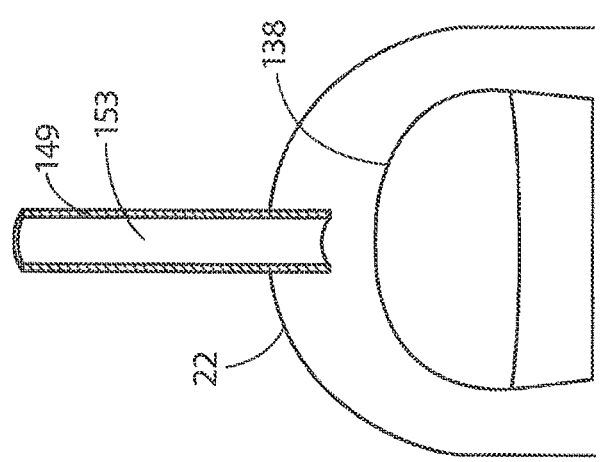

In FIG. 18A, a cannula 149 is shown extending into a shoulder 22. Cannula 149 defines a lumen 153. A distal end of cannula 149 is located proximate a target tissue 138. The distal end of cannula 149 defines a distal opening that fluidly communicates with lumen 153.

In FIG. 18B, a locating guide 125 is shown extending through lumen 153 defined by cannula 149. Some methods in accordance with the present disclosure may include the step of advancing the distal end of a locating guide through a cannula. In the embodiment of FIG. 18B, a distal portion of locating guide 125 is disposed in target tissue 138. In some useful embodiments, the distal portion of locating guide 125 includes a barb. When this is the case, the barb may help maintain the position of the distal end of locating guide 125 in the target tissue In FIG. 18C, a sheet-like implant 50 is shown disposed about locating guide 125. Some methods in accordance with the present disclosure may include the step of inserting a locating guide through a sheet-like implant. Some of these methods may also include the step of advancing the sheet-like implant over the locating guide toward a target tissue.

In FIG. 18D, a delivery aid 129 is shown disposed about locating guide 125. Some methods in accordance with the present disclosure may include the step of inserting the proximal end of a locating guide 125 into a distal aperture of a delivery aid 129. When this is the case, the delivery aid 129 may be advanced over locating guide 125 for urging a sheet-like implant 50 toward a target tissue (e.g., target tissue 138). In this way, delivery aid 129 may be used to urge sheet-like implant 50 in a longitudinal direction along locating guide 125. In some applications, delivery aid 129 may also be used to hold sheet-like implant 50 against a target tissue.

In the embodiment of FIG. 18E, sheet-like implant 50 is disposed in a lumen 153 defined by cannula 149. By comparing FIG. 18E and FIG. 18D, it will be appreciated that sheet-like implant 50 has been pushed distally into lumen 153. In the embodiment of FIG. 18E, sheet-like implant 50 has been folded into a compact configuration. Sheet-like implant 50 is shown overlaying the implant expander of delivery aid 129 in FIG. 18E. In the exemplary embodiment of FIG. 18E, the implant expander is urged to assume a first compact configuration as the implant expander and sheet-like implant 50 are advanced into lumen 153.

In the exemplary embodiment of FIG. 18F, sheet-like implant 50 is shown overlaying target tissue 138. Some methods in accordance with the present detailed description include the step of passing a sheet-like implant through a cannula. In the exemplary embodiment of FIG. 18F, for example, sheet-like implant 50 may be pushed through cannula 149 using delivery aid 129. Delivery aid 129 may also be used to hold sheet-like implant 50 against target tissue 138 while a surgeon attaches sheet-like implant 50 to target tissue 138.

In FIG. 18G, a fixation tool shaft 72 of a fixation tool 70 is shown extending through cannula 149. In FIG. 18G, a distal end of fixation tool shaft 72 is disposed proximate sheet-like implant 50. One or more staples may be disposed inside fixation tool shaft 72. Some methods in accordance with the present detailed description include the step of passing a staple through a cannula. In the exemplary embodiment of FIG. 18G, for example, a staple may be passed through cannula 149 while the staple resides in fixation tool shaft 72.

In the exemplary embodiment of FIG. 18H, sheet-like implant 50 is fixed to target tissue 138 by a plurality of staples 74. In some exemplary methods, a plurality of staples may be applied to a sheet-like implant and a target tissue using a fixation tool. The fixation tool may then be withdrawn from the body of the patient. With reference to FIG. 18H, it will be appreciated that delivery aid 129 has been withdrawn from shoulder 22 and locating guide 125 remains in the position shown in FIG. 18H.

In the exemplary embodiment of FIG. 18I, locating guide 125 has been withdrawn from shoulder 22. Some useful methods in accordance with the present detailed description, include the use of a locating guide including a temporary fixation mechanism located proximate its distal end. These exemplary methods may also include the use of a locating guide removal tool to aid in withdrawing the locating guide from the body of the patient. In FIG. 18I, a plurality of staples 74 can be seen fixing sheet-like implant 50 to target tissue 138.

Figure 19:
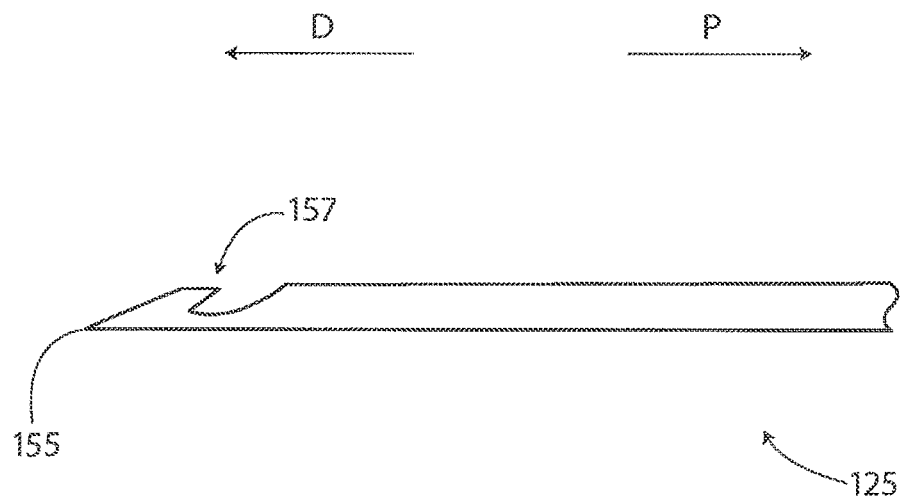
FIG. 19 is a plan view showing a locating guide included in the kit of FIG. 16.

FIG. 19 is a plan view showing a locating guide 125. With reference to FIG. 19, it will be appreciated that locating guide 125 has a point 155 at its distal end. In the embodiment of FIG. 19, locating guide 125 includes a barb 157 near its distal end. In FIG. 19, point 155 is shown pointing in a distal direction D and barb 157 is shown pointing in a proximal direction P.

Figure 20:
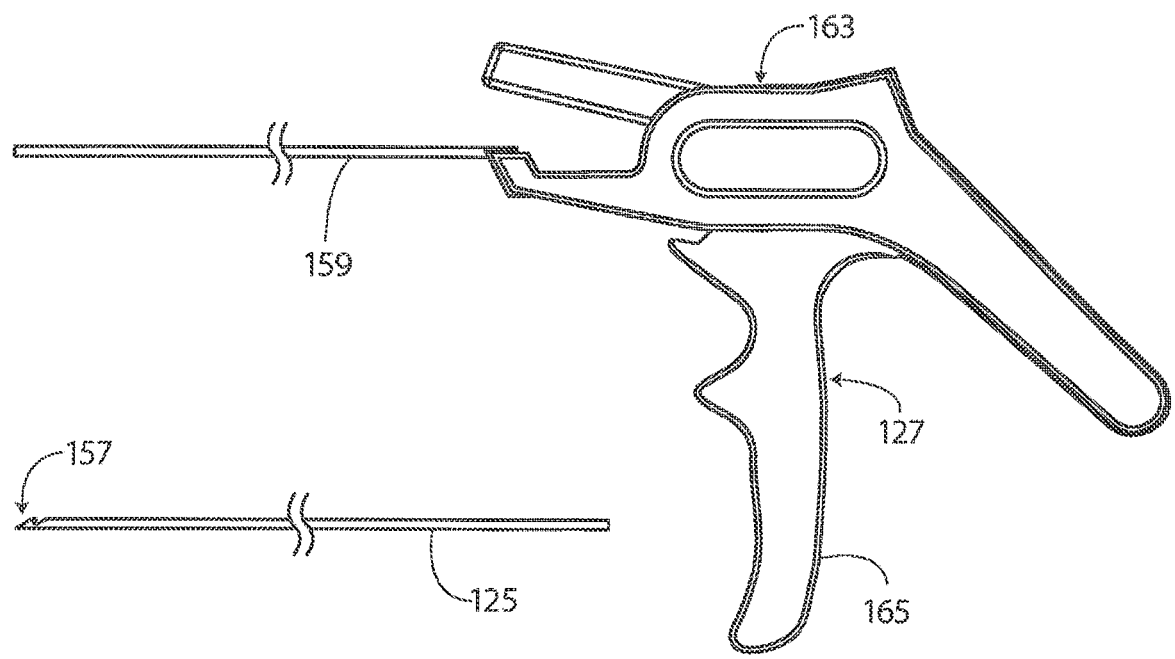
FIG. 20 is a plan view showing a locating guide removal tool included in the kit of FIG. 16.

FIG. 20 is a plan view showing a locating guide removal tool 127. Locating guide removal tool 27 may be used, for example, to remove a locating guide 125 from a target tissue. In the embodiment of FIG. 20, locating guide removal tool 127 includes a tubular body 159 that is fixed to a grip 163. In operation, tubular body 159 is advanced over the proximal end of a locating guide so that a portion of the locating guide extends into a lumen defined by tubular body 159. Locating guide removal tool 127 may then be used to grasp a proximal portion of the locating guide and produce relative motion between the locating guide and tubular body 159.

In the embodiment of FIG. 20, a lever 165 is pivotably coupled to grip 163. Relative motion between locating guide 125 and tubular body 159 can be produced by rotating lever 165 relative to grip 163 when locating guide removal tool 127 is grasping the proximal portion of locating guide 125. This relative motion can be used to advance tubular body 159 over the barb 157 of locating guide 125. Locating guide 125 may be withdrawn from the body of the patient while tubular body 159 is covering barb 157.

While exemplary embodiments of the present invention have been shown and described, modifications may be made, and it is therefore intended in the appended claims and subsequently filed claims to cover all such changes and modifications which fall within the true spirit and scope of the invention.

What is claimed is:

1. An implant delivery system adapted to deliver a sheet-like implant to a target tissue, the implant delivery system comprising:
    a delivery shaft extending along a longitudinal axis, the delivery shaft including a proximal end and a distal end;
    an implant expander including a body portion and a plurality of flexible legs extending from the body portion, the body portion coupled to the distal end of the delivery shaft, wherein the plurality of flexible legs are configured to move between a compact configuration and an expanded configuration;
    a sheet-like implant having an upper surface facing the implant expander, a lower surface configured to be positioned against the target tissue, and a thickness measured from the upper surface to the lower surface;
    wherein the plurality of flexible legs define a concave surface extending across the upper surface of the sheet-like implant in the expanded configuration; and
    a plurality of retainers extending from the flexible legs and penetrating into the sheet-like implant to retain the sheet-like implant thereto.

2. The implant delivery system of claim 1, further comprising a projection extending distally from the body portion of the implant expander along the longitudinal axis.

3. The implant delivery system of claim 2, wherein the projection comprises a pointed distal tip pointing in a distal direction along the longitudinal axis.

4. The implant delivery system of claim 3, wherein the pointed distal tip is configured to penetrate into the target tissue.

5. The implant delivery system of claim 3, wherein the pointed distal tip penetrates through the sheet-like implant in the expanded configuration.

6. The implant delivery system of claim 1, wherein the plurality of flexible legs are elastically deformed in the compact configuration.

7. An implant delivery system adapted to deliver a sheet-like implant to a target tissue, the implant delivery system comprising:
    a delivery sheath having a lumen therein;
    a delivery shaft movably disposed in the lumen of the delivery sheath along a longitudinal axis of the delivery shaft, the delivery shaft including a proximal end and a distal end;
    an implant expander including a body portion and a plurality of flexible legs extending from the body portion, the body portion coupled to the distal end of the delivery shaft, wherein the plurality of flexible legs are configured to move between a compact configuration when constrained within the delivery sheath and an expanded configuration when deployed from the delivery sheath;
    a sheet-like implant having an upper surface facing the implant expander, a lower surface configured to be positioned against the target tissue, and a thickness measured from the upper surface to the lower surface;
    wherein the plurality of flexible legs define a concave surface extending along the upper surface of the sheet-like implant in the expanded configuration; and
    a plurality of retainers extending from the flexible legs and penetrating into the sheet-like from the upper surface of the sheet-like implant to retain the sheet-like implant thereto.

8. The implant delivery system of claim 7, further comprising a projection extending distally from the body portion of the implant expander along the longitudinal axis.

9. The implant delivery system of claim 8, wherein the projection comprises a pointed distal tip pointing in a distal direction along the longitudinal axis.

10. The implant delivery system of claim 9, wherein the pointed distal tip is configured to penetrate into the target tissue.

11. The implant delivery system of claim 9, wherein the pointed distal tip penetrates through the sheet-like implant in the expanded configuration.

12. The implant delivery system of claim 8, wherein the projection is configured to temporarily hold the sheet-like implant in position against the target tissue.

13. The implant delivery system of claim 7, wherein the plurality of flexible legs are elastically deformed in the compact configuration.

14. The implant delivery system of claim 7, wherein the plurality of retainers are located near free ends of the plurality of legs.

15. The implant delivery system of claim 14, wherein the plurality of retainers curve toward the free ends of the plurality of legs.

16. The implant delivery system of claim 7, wherein the plurality of retainers have a hook shape.

17. A method of deploying a sheet-like implant comprising:
    positioning an implant delivery device proximate a target tissue site, the implant delivery device comprising:
    a delivery shaft having a proximal end and a distal end;
    an implant expander, mounted to the distal end of the delivery shaft, the implant expander including a body portion, a plurality of leg portions extending from the body portion, and a plurality of retainers extending from the flexible legs;
    a sheath having a proximal end and a distal end and defining a lumen, wherein at least a portion of the delivery shaft is slidably disposed in the lumen; and
    a sheet-like implant disposed at least partially within the sheath in a compact configuration covering at least a portion of the implant expander, with the plurality of retainers penetrating into the sheet-like implant;
    advancing the delivery shaft relative to the sheath to cause the implant expander to advance through a distal opening of the sheath, wherein after advancing through the distal opening of the sheath, the implant expander causes the sheet-like implant to transition from the compact configuration to an expanded configuration, the plurality of flexible legs defining a concave surface extending along an upper surface of the sheet-like implant in the expanded configuration.

18. The method of claim 17, wherein the implant expander further comprises a distal tip extending distally from a distal surface of the body portion of the implant expander, and the method further comprises:
    causing the distal tip to penetrate the target tissue in order to temporarily hold the sheet-like implant in position relative to the target tissue; and
    attaching the sheet-like implant to the target tissue.

19. The method of claim 17, further comprising inserting one or more sutures through the sheet-like implant.

20. The method of claim 19, further comprising withdrawing the implant expander subsequent to insertion of the one or more sutures.

\* \* \* \* \*